US006919370B2

(12) United States Patent  
Chen

(10) Patent No.: US 6,919,370 B2  
(45) Date of Patent: Jul. 19, 2005

(54) PHARMACEUTICAL FORMULATIONS COMPRISING PACLITAXEL, DERIVATIVES, AND PHARMACEUTICALLY ACCEPTABLE SALTS THEREOF

(75) Inventor: Hongming Chen, Acton, MA (US)

(73) Assignee: TransForm Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 10/343,780

(22) PCT Filed: Nov. 20, 2001

(86) PCT No.: PCT/US01/43306

§ 371 (c)(1),
(2), (4) Date: Feb. 3, 2003

(87) PCT Pub. No.: WO02/43765

PCT Pub. Date: Jun. 6, 2002

(65) Prior Publication Data

US 2003/0207936 A1 Nov. 6, 2003

Related U.S. Application Data

(60) Provisional application No. 60/253,640, filed on Nov. 28, 2000, and provisional application No. 60/272,117, filed on Feb. 28, 2001.

(51) Int. Cl.$^7$ ............................................. A61K 31/335
(52) U.S. Cl. ..................................................... 514/449
(58) Field of Search ................................ 514/320, 449, 514/510, 517, 458

(56) References Cited

U.S. PATENT DOCUMENTS

| 3,070,499 | A | | 12/1962 | Mullins et al. |
| 3,220,923 | A | | 11/1965 | Scholtan |
| 3,824,263 | A | | 7/1974 | Umbach |
| 3,864,370 | A | | 2/1975 | Yamashita et al. |
| 4,366,151 | A | | 12/1982 | Oppenlaender et al. |
| 4,572,915 | A | | 2/1986 | Crooks |
| 4,814,470 | A | | 3/1989 | Colin et al. |
| 4,942,184 | A | | 7/1990 | Haugwitz et al. |
| 4,960,790 | A | | 10/1990 | Stella et al. |
| 5,156,842 | A | | 10/1992 | Mulligan |
| 5,157,049 | A | | 10/1992 | Haugwitz et al. |
| 5,254,580 | A | | 10/1993 | Chen et al. |
| 5,281,727 | A | | 1/1994 | Carver et al. |
| 5,364,631 | A | | 11/1994 | Janoff et al. |
| 5,387,579 | A | | 2/1995 | Meybeck et al. |
| 5,391,385 | A | | 2/1995 | Seybold |
| 5,403,858 | A | | 4/1995 | Bastard et al. |
| 5,438,072 | A | | 8/1995 | Bobee et al. |
| 5,504,102 | A | | 4/1996 | Agharkar et al. |
| 5,656,618 | A | | 8/1997 | Meybeck et al. |
| 5,681,846 | A | | 10/1997 | Trissel |
| 5,698,582 | A | * | 12/1997 | Bastart et al. ............... 514/449 |
| 5,733,888 | A | | 3/1998 | Carver et al. |
| 5,877,205 | A | * | 3/1999 | Andersson ................... 514/449 |
| 5,897,876 | A | | 4/1999 | Rudnic et al. |
| 5,925,776 | A | | 7/1999 | Nikolayev et al. |
| 5,952,001 | A | | 9/1999 | Meybeck et al. |
| 5,965,603 | A | | 10/1999 | Johnson et al. |
| 5,972,992 | A | | 10/1999 | Carver et al. |
| 5,977,164 | A | | 11/1999 | Carver et al. |
| 6,136,846 | A | | 10/2000 | Rubinfeld et al. |
| 6,140,359 | A | | 10/2000 | Carver et al. |
| 6,248,363 | B1 | * | 6/2001 | Patel et al. .................. 424/497 |
| 6,267,985 | B1 | * | 7/2001 | Chen et al. .................. 424/451 |
| 6,306,894 | B1 | | 10/2001 | Carver et al. |
| 6,660,286 | B1 | | 12/2003 | Lambert et al. |
| 2001/0029264 | A1 | * | 10/2001 | McChesney-Harris ...... 514/449 |

FOREIGN PATENT DOCUMENTS

| AU | 667142 | 6/1994 | |
| DE | 694 178 | 6/1940 | |
| DE | 1 235 452 | 6/1971 | |
| DE | 1 440 275 | 6/1976 | |
| EP | 0 295 941 | 12/1988 | |
| EP | 0 428 376 | 5/1991 | |
| EP | 0 505 047 | 9/1992 | |
| EP | 0 522 936 | 1/1993 | |
| EP | 0 522 937 | 1/1993 | |
| EP | 0 674 510 | 6/1994 | |
| WO | 90/08537 | 8/1990 | |
| WO | 90/10443 | 9/1990 | |
| WO | 94/12198 | 6/1994 | |
| WO | 97 30695 | 8/1997 | |
| WO | WO98/30205 | 7/1998 | |
| WO | 99 45918 | 9/1999 | |
| WO | WO 9945918 A1 * | 9/1999 | ......... A61K/31/335 |
| WO | 99 49848 | 10/1999 | |
| WO | 00 03753 | 1/2000 | |
| WO | 00 40238 | 7/2000 | |
| WO | WO00/71163 A1 | 11/2000 | |
| WO | 00 71163 | 11/2000 | |
| WO | 01 01960 | 1/2001 | |
| WO | WO01/22937 A1 | 4/2001 | |
| WO | 01 30448 | 5/2001 | |
| WO | 02 43765 | 6/2002 | |

OTHER PUBLICATIONS

Chen et al., "A High–Throughput Combinatorial Approach for the Discovery of a Cremophor EL–Free Paclitaxel Formulation", Pharmaceutical Research, vol. 20, No. *, Aug. 2003.

Trissel, Lawrence A., "Handbook on Injectable Drugs", American Society of Hospital Pharmacists, Inc. 1988.

(Continued)

Primary Examiner—Raymond J. Henley, III
(74) Attorney, Agent, or Firm—Paul Burgess; Christopher Olson

(57) ABSTRACT

The invention concerns paclitaxel solubilizers and formulations thereof with a high propensity to dissolve paclitaxel. The formulations of the invention reduce or obviate the need for the disadvantageous excipient Cremophor® EL. The formulations of the invention are useful for administering paclitaxel, its derivatives, or pharmaceutically acceptable salts or such derivatives to patients in need thereof. The formulations of the invention are suitable for parenteral, oral, local, or transdermal administration to mammals including humans, particularly for intravenous delivery.

28 Claims, 4 Drawing Sheets

OTHER PUBLICATIONS

Wauch, Wanda A., "Stability, Compatibility, and Plasticizer Extraction of (NSC–125973) Injection Diluted in Infusion Solutions and Stored in Various Containers", AJHP, vol. 48, Jul. 1991.

"Cremophor EL" Technical Leaflet, BASF Ludwigshafen, Germany, (no date available).

"Polyoxyl 35 Castor Oil", "Polyoxyl 40 Hydrogenated Castor Oil", The United States Pharmacopeia, United States Pharmacopeial Convention, Inc., Rockville, MD, Jan. 1, 1995.

Taxol Specification Sheet, Physicians Desk Reference, 1994.

Taxol Specification Sheet, Physicians Desk Reference, 1995.

Taxol Specification Sheet, Physicians Desk Reference, 1996.

Taxol Specification Sheet, Physicians Desk Reference, 1997.

Taxol Specification Sheet, Physicians Desk Reference, 1998.

Taxol Specification Sheet, Physicians Desk Reference, 2000.

Castor Oil Specification Sheet, The United States Pharmacopeia, United States Pharmacopeial Convention, Inc., Rockville, MD, Jan. 1, 2000.

Castor Oil, Merck Index, $12^{th}$ Edition, pp. 311–312, (1999).

Kibbe, Arthur, "Polyoxethylene Castor Oil Derivatives", Handbook of Pharmaceutical Excipients, Pennsylvania, pp. 412–415, (no date available).

Magri, Neal F., "Modified Taxols. Oxidation Products of Taxol", Department of Chemistry, VA Polytechnic Institute and State University, VA, Sep. 26, 1985, pp. 797–802.

Mathew, Abraham E., "Synthesis and Evaluation of Some Water–Soluble Prodrugs and Derivatives of Taxol with Antitumor Activity", Departments of Pharmaceutical Chemistry and Biochemistry, University of Kansas, Jan. 11, 1991.

Ringel, Israel, "Taxol is Converted to 7–Epitaxol, a Biologically Active Isomer, in Cell Culture Medium", Department of Molecular Pharmacology and Cell Biology, Albert Einstein College of Medicine, NY, Apr. 13, 1987.

Richheimer, Steven L. et al., "High Performance Liquid Chromatographic Assay of Taxol" Analytical Chemistry, vol. 64, No. 20, Oct. 15, 1992.

Rowinsky, Eric K., "Taxol: A Novel Investigational Antimicrotubule Agent", Journal of the National Cancer Institute, vol. 82, No. 15, Aug. 1, 1990.

Tarr, Bryan D. et al., "A New Parenteral Vehicle for the Administration of Some Poorly Water Soluble Anti–Cancer Drugs", Journal of Parenteral Science and Technology, vol. 41, No. 1, Jan–Feb. 1987.

Drori, Stavit et al., "Potentiation of Anticancer Cytotoxicity by Multidrug–Resistance Chemosensitizers Involves Alterations in Membrane Fluidity Leading to Increased Membrane Permeability", European Journal of Biochemistry, 228, pp. 1020–1029, (no date available).

Dordunoo, Stephen K. et al., "Solubility and Stability of Taxol: Effects of Buffers and Cyclodextrins", International Journal of Pharmaceutics, 133, (1996) pp. 191–201.

Longnecker, Stephen M. et al., "High–Performance Liquid Chromatographic Assay for Taxol in Human Plasma and Urine and Pharmacokinetics in Phase I Trial", Cancer Treatment Reports, vol. 71, No. 1, Jan. 1987.

Legha, Sewa S., "Phase I Study of Taxol Using a 5–Day Intermittent Schedule", Journal of Clinical Oncology, vol. 4, No. 5, 1986, pp. 762–766.

Kingston, David G. I. Et al., "Synthesis and Structure–Activity Relationships of Taxol Derivatives as Anticancer Agents", New Trends in Natural Products Chemistry 1986, Studies in Organic Chemistry, vol. 26.

Kingston, David G. I., "The Chemistry of Taxol", Pharmaceutical Ther. vol. 52, pp. 1–34, 1991.

Kagel, J.R., et al., Taxol Stability in Aqueous Solutions or In Organic/Aqueous Cosolvents, Department of Pharmaceutical Chemistry, University of Kansas, APQ 1232., (no date available).

* cited by examiner

PHARMACEUTICAL FORMULATIONS COMPRISING PACLITAXEL, DERIVATIVES, AND PHARMACEUTICALLY ACCEPTABLE SALTS THEREOF

This application claims the benefit of U.S. Provisional Application No. 60/253,640 filed Nov. 28, 2000, and U.S. Provisional Application No. 60/272,117 filed Feb. 28, 2001, which are incorporated by reference herein in their entirety.

1. FIELD OF THE INVENTION

The present invention is directed to excipients or combinations thereof suitable for preparing a formulation containing a pharmaceutical agent. More particularly, the invention is directed to stable and efficacious pharmaceutical formulations comprising paclitaxel, derivatives, and pharmaceutically acceptable salts thereof.

2. BACKGROUND OF THE INVENTION

Pharmaceuticals are rarely distributed as pure compounds because of problems with, among others, stability, solubility, and bioavailability of the pharmaceutical itself (i.e., the active), and in most cases, are administered in a pharmaceutical formulation comprising the active, and other components, such as excipients, binders, diluents, and other delivery vehicles or systems. It is well documented that physical and chemical properties, such as stability, solubility, dissolution, permeability, and partitioning of most pharmaceuticals are directly related to the medium in which they are administered. And, in turn, the physical and chemical properties of drug-in-formulation mixtures affect the pharmacological and pharmacokinetic properties, such as absorption, bioavailability, metabolic profile, toxicity, and potency. Such effects are caused by interactions between the formulation's components and the pharmaceutical and/or interactions between the components themselves. Other properties influenced by the formulation in which a pharmaceutical is administered include mechanical properties, such as compressibility, compactability, and flow characteristics and sensory properties, such as taste, smell, and color. Thus, discovery of pharmaceutical formulations that optimize bioavailability and duration of action of the pharmaceutical and minimize undesirable properties is an important part of pharmaceutical development and research. For a general review of the subject of formulations see Howard, *Introduction to Pharmaceutical Dosage Forms*, Lea & Febiger, Philadelphia Pa., 4$^{th}$ ed., 1985; *Remington: the Science and Practice of Pharmacy*, Alfonso R. Gennaro ed., Mack Publishing Co. Easton, Pa., 19th ed., 1995, Chapter 83.

Formulation development is normally a tedious process, where many variables must be separately assessed. For example, if the formulation contains a pharmaceutical characterized by poor solubility, the solubility of the pharmaceutical in a range of salt concentrations; pHs; excipients; and pharmaceutical concentrations must be prepared and tested to find interactions between the pharmaceutical and excipients or interactions between excipients that affect the pharmaceutical's solubility. While some general rules exist, the effect of excipients and combinations of excipients on the physical and chemical properties of the pharmaceutical are not easily predicted. Moreover, there are over 3,000 excipients to choose from when designing pharmaceutical formulations, each having differing degrees and types of interactions with each other and with the pharmaceutical. (For a listing of generally regarded as safe (GRAS) excipients see the Code of Federal Regulations (CFR) at 21 CFR 182 and 21 CFR 184). Because of the many variables involved, industry does not have the time or resources to identify, measure, or exploit interactions between excipients and pharmaceuticals and thus cannot provide optimized pharmaceutical formulations tailored to the particular pharmaceutical. Such work would require testing hundreds to thousands of formulations a day. Assuming three hundred substances are to be tested for efficacy as excipients in a pharmaceutical formulation, even with no variations in concentrations and no physical or chemical property variations, the number of possible combinations is enormous: when two of the substances are selected, there are 45,150 possible combinations, for three components there are 4,545,100 combinations, and for four components, there are 344,291,325 possible combinations. The complexity is increased when the relative ratio of each component is considered. Unfortunately, technologies that can make many pharmaceutical-excipient combinations at the same time, then automatically feed each combination into a system for identifying the combinations that have optimized properties are not known. Today, since it is more cost effective, most pharmaceuticals are distributed and administered in the standard, un-optimized formulations, see e.g., *Allen's Compounded Formulations: U.S. Pharmacists Collection* 1995 to 1998, ed. Lloyd Allen.

Paclitaxel is presently available in the United States only as a non-aqueous sub-optimal formulation concentrate for intravenous injection. An intravenous dosage regimen of 135 mg/m$^2$ paclitaxel is recommended for previously untreated patients with carcinoma of the ovary, given every three weeks. Similar dosage regimens are recommend for other carcinomas. Paclitaxel is practically insoluble in water. The commercially-available paclitaxel formulation (Bristol-Myers Squibb) comprises 6 mg/ml of paclitaxel dissolved in Cremophor® EL (PEG-35 castor oil, polyoxyethylated castor oil) and dehydrated ethanol (50% v/v). Similar formulations are sold by other manufacturers, for example, IVAX Co. Before intravenous injection, the commercial dose must be diluted to a final concentration of 0.3 to 1.2 mg/ml prior to injection. Recommended diluents are 0.9% aqueous sodium chloride, 5% aqueous dextrose, or 0.9% sodium chloride 5% dextrose aqueous solution, or 5% dextrose in Ringer's injection (The Physician's Desk Reference, 54th edition, 881–887,Medical Economics Company (2000); Goldspiel 1994 *Ann. Pharmacotherapy* 28:S23–26, both of which are incorporated herein by reference).

In general, the amount of Cremophor® EL necessary to deliver the required doses of paclitaxel is significantly higher than that administered with other drugs currently formulated in Cremophor® EL. This is a particular problem since several toxic effects have been attributed to Cremophor® EL, including vasodilation, dyspnea, and hypotension. This vehicle has also been shown to cause serious hypersensitivity in laboratory animals and humans (Weiss et al., 1990, *J. Clin. Oncol.* 8:1263–1268). In fact, the maximum dose of paclitaxel that can be administered to mice by i.v. bolus injection is dictated by the acute lethal toxicity of the Cremophor® EL vehicle (Eiseman et al., 1994, *Cancer Chemother. Pharmacol.* 34:465–471).

In addition, Cremophor® EL is known to leach phthalate plasticizers such as di(2-ethylhexyl)phthalate (DEHP) from the polyvinylchloride bags and intravenous administration tubing. DEHP is known to cause hepatotoxicity in animals and is carcinogenic in rodents. Upon dilution with infusion solutions, paclitaxel Cremophor® EL formulations can result in particulate formation. In addition, fibrous precipitates of unknown composition can form in the concentrate during storage for extended periods of time. It is generally believed that the precipitates are degradation by-products of either components in the solvent or paclitaxel. In such case, filtration of the diluted Cremophor® EL/ethanol/paclitaxel formulation is necessary during administration (Goldspiel 1994 *Ann. Pharmacotherapy* 28:S23–26).

It has further been reported, in U.S. Pat. No. 5,504,102, that commercial grade Cremophor® EL with ethanol as a co-solvent, although effective in dissolving paclitaxel, produces injection formulations that exhibit instability over extended periods of time. In particular, pharmaceutical formulations of paclitaxel in a co-solvent of 50:50 by volume of dehydrated ethyl alcohol and commercial grade Cremophor® EL exhibit a loss of potency of greater than 60% after storage for 12 weeks at 50° C. The loss of potency is attributed to the degradation of paclitaxel during storage. Other disadvantages of. Cremophor® EL have been reported.

Some efforts have focused on limiting or eliminating Cremophor® EL by preparing paclitaxel derivatives having improved aqueous solubility over paclitaxel. Research in this area includes preparation of 2'-succinate- and aminoacid-ester prodrugs of paclitaxel (see e.g., Deutsch et al., 1989, *J. Med. Chem.*, 32:788–792; Matthew et al., 1992, *J. Med. Chem.* 35:145–151). In other efforts, Greenwald et al. reported the synthesis of highly water-soluble 2' and 7-polyethylene glycol esters of paclitaxel (Greenwald et al., 1994, *Bioorganic & Medicinal Chemistry Letters* 4:2465–2470), however, no data concerning the in-vivo antitumor activity of these compounds were reported (Greenwald et al., 1995, *J. Org. Chem.* 60:331–336). Others attempts to solve paclitaxel's aqueous-solubility problems have involved microencapsulation of paclitaxel in both liposomes and nanospheres (Bartoni et al., 1990, *J. Microencapsulation* 7:191–197). The liposome formulation was reported to be as effective as free paclitaxel, however, only liposome formulations containing less than 2% paclitaxel were physically stable (Sharma et al., 1994, *Pharm. Res.* 11:889–896). There is a need, therefore, for formulations comprising paclitaxel, derivatives, and pharmaceutically acceptable salts thereof that can deliver therapeutically effective amounts of paclitaxel and derivatives thereof that overcome the disadvantages caused by paclitaxel's insolubility and the disadvantages of Cremophor® EL.

3. SUMMARY OF THE INVENTION

In a preferred embodiment, the invention concerns paclitaxel solubilizers and formulations thereof with a high propensity to promote dissolution of paclitaxel or that stabilize aqueous paclitaxel solutions. The formulations of the invention are useful for administering paclitaxel, its derivatives, or pharmaceutically acceptable salts of such derivatives to patients in need thereof. The formulations of the invention are suitable for parenteral, oral, local, or transdermal administration to mammals including humans, particularly for intravenous delivery.

More generally, the paclitaxel solubilizers of the invention or mixtures thereof can replace the disadvantageous excipient Cremophor® EL as a solubilizing excipient in existing pharmaceutical formulations comprising hydrophobic pharmaceuticals or the need to use Cremophor® EL with such pharmaceuticals. Thus, the formulations of the invention are suitable to administer any drug for which Cremophor® EL is now used or would today be the first choice as an aqueous solubilization excipient. The formulations of the invention are particularly suitable to administer paclitaxel and derivatives thereof.

In one embodiment, the invention concerns a pharmaceutical formulation for administration to a mammal comprising:
  (a) paclitaxel, a derivative, or a pharmaceutically acceptable salt thereof; and
  (b) one or more of a PEG-glyceryl fatty ester, a quaternary ammonium salt or a PEG-fatty alcohol.

In this embodiment, preferably, the quaternary ammonium salt is benzalkonium chloride, benzethonium chloride, or cetrimide; the PEG-glyceryl fatty ester is PEG-glyceryl monooleate or PEG-glyceryl monolaurate; and the PEG-fatty alcohol is an octoxynol, an oleth, or a laureth.

In another embodiment, the invention concerns a pharmaceutical formulation for administration to a mammal comprising:
  (a) paclitaxel, a derivative, or a pharmaceutically acceptable salt thereof; and
  (b) two or more of a PEG-vitamin E, a quaternary ammonium salt, a PEG-monoacid fatty ester, a PEG-glyceryl fatty ester, a polysorbate, or a PEG-fatty alcohol.

Preferably, the PEG-vitamin E is tocophersolan; the quaternary ammonium salt is benzalkonium chloride, benzethonium chloride, or cetrimide; the PEG-monoacid fatty ester is PEG-20 monooleate, PEG-20 monolaurate, PEG-20 monostearate; the PEG-glyceryl fatty ester is PEG-20 glyceryl monooleate, PEG-20 glyceryl monostearate, or PEG-20 glyceryl monolaurate; the polysorbate is polysorbate 20 or polysorbate 80; and the PEG-fatty alcohol is an octoxynol, an oleth, or a laureth. A preferred octoxynol is octoxynol-9 and preferred laureth is laureth-23.

In a separate embodiment, the formulations of the invention do not contain a quaternary ammonium salt.

In one preferred aspect of this embodiment, the paclitaxel solubilizers are a PEG-vitamin E and one or more of a PEG-monoacid fatty ester, the PEG-glyceryl fatty ester, a polysorbate, or a PEG-fatty alcohol.

In another preferred aspect of this embodiment, the paclitaxel solubilizers are a quaternary ammonium salt and one or both of a polysorbate or a PEG-fatty alcohol.

In still another preferred aspect of this embodiment, the paclitaxel solubilizers are a PEG-monoacid fatty ester and one or more of a PEG-vitamin E, the PEG-glyceryl fatty ester, a polysorbate, or a PEG-fatty alcohol.

In another embodiment, the paclitaxel solubilizers are a PEG-glyceryl fatty ester and one or more of the PEG-vitamin E, the PEG-monoacid fatty ester, or the polysorbate.

In yet another preferred aspect of this embodiment, the paclitaxel solubilizers are a polysorbate and one or more of a quaternary ammonium salt, a PEG-monoacid fatty ester, a PEG-glyceryl fatty ester, or a PEG-fatty alcohol.

In another preferred aspect of this embodiment, the paclitaxel solubilizers are a PEG-fatty alcohol and one or more of a PEG-vitamin E, a quaternary ammonium salt, a PEG-monoacid fatty ester, or a polysorbate.

In another embodiment, the invention concerns a pharmaceutical formulation for administration to a mammal comprising:
  (a) paclitaxel, a derivative, or a pharmaceutically acceptable salt thereof; and
  (b) PEG-400 and one or more of a PEG-vitamin E, a quaternary ammonium salt, a PEG-monoacid fatty ester, a PEG-glyceryl fatty ester, a polysorbate, or a PEG-fatty alcohol.

In a separate embodiment, the invention relates to a method of treating cancer or other conditions treatable by paclitaxel in a mammal comprising administering to said mammal a therapeutically effective amount of a formulation of the invention.

In still another embodiment, the formulations of the invention can be independent of paclitaxel, a derivative, or a salt thereof. Such formulations are referred to herein as paclitaxel free formulations of the invention and can be used to solubilize and administer any pharmaceutical. Paclitaxel free formulations of the invention are particularly useful as a replacement for cremophor and similar excipients in pharmaceutical formulations currently comprising them.

In another embodiment, the invention relates to a pharmaceutical formulation suitable for administration to a human consisting essentially of:
(a) paclitaxel, a derivative, or a pharmaceutically acceptable salt thereof;
(b) one or more of a PEG-vitamin E, a quaternary ammonium salt, a PEG-monoacid fatty ester, a PEG-glyceryl fatty ester, a polysorbate, or a PEG-fatty alcohol; and
(c) ethanol,
wherein said formulation is free of cremophor and is suitable for dissolution or reconstitution with an aqueous medium into a particulate-free solution suitable for parenteral administration.

In yet another embodiment, the invention relates to a pharmaceutical formulation suitable for administration to a human consisting essentially of:
(a) paclitaxel, a derivative, or a pharmaceutically acceptable salt thereof;
(b) two or more of a PEG-vitamin E, a quaternary ammonium salt, a PEG-monoacid fatty ester, a PEG-glyceryl fatty ester, a polysorbate, or a PEG-fatty alcohol; and
(c) ethanol,
wherein said formulation is free of cremophor and is suitable for dissolution or reconstitution with an aqueous medium into a particulate-free solution suitable for parenteral administration.

In another embodiment, the invention relates to arrays and methods for high-throughput preparation of a large number of excipient/active combinations (e.g., thousands to hundreds of thousands), at varying concentrations, at the same time, and high-throughput testing thereof. An example of such a process is described in the Examples section herein. Such methods allow detection or measurement of interactions between formulation components (e.g., excipients) and actives; between multiple formulation components; or between multiple actives. Once such interactions or lack of interactions are identified, the active can be "retrofitted" into an optimal formulation for pharmaceutical administration.

The invention thus encompasses the high-throughput testing of formulations comprising paclitaxel, a derivative, or a salt thereof in order to determine the overall optimal formulations, or to optimize any particular desired property or results, e.g., bioavailability, potency, release, stability, and the like; or both. To applicant's knowledge, a systematic, high-throughput method for formulation generation, screening, testing, and analysis, has not been published prior to this invention.

In this regard, another embodiment of the invention concerns an array of samples, each sample comprising paclitaxel, a derivative, or a pharmaceutically acceptable salt thereof and at least one formulation component, wherein each sample differs from any other sample with respect to at least one of:
(i) the identity of the formulation component, or
(ii) the ratio of the paclitaxel, the derivative, or the pharmaceutically acceptable salt thereof to the formulation component.

In still another embodiment, the invention relates to a method to find a pharmaceutical formulation suitable to administer paclitaxel to mammal, comprising:
(a) preparing an array of samples, each sample comprising paclitaxel, a derivative, or a pharmaceutically acceptable salt thereof and a formulation component, wherein each sample differs from any other sample with respect to at least one of:
(i) the identity of the formulation component,
(ii) the ratio of the paclitaxel, the derivative, or the pharmaceutically acceptable salt thereof to the formulation component; and
(b) testing each sample for a property.

In still another embodiment, the invention relates to a particulate-free pharmaceutical formulation suitable for parenteral administration to a mammal comprising about 0.2 mg/ml to about 3.0 mg/ml of paclitaxel in a non-cremophor aqueous-based solution, where per mg of the paclitaxel in the formulation the amount of water is about 4.5 ml to about 0.3 ml.

3.1 BRIEF DESCRIPTION OF THE DRAWINGS

Figure 1:
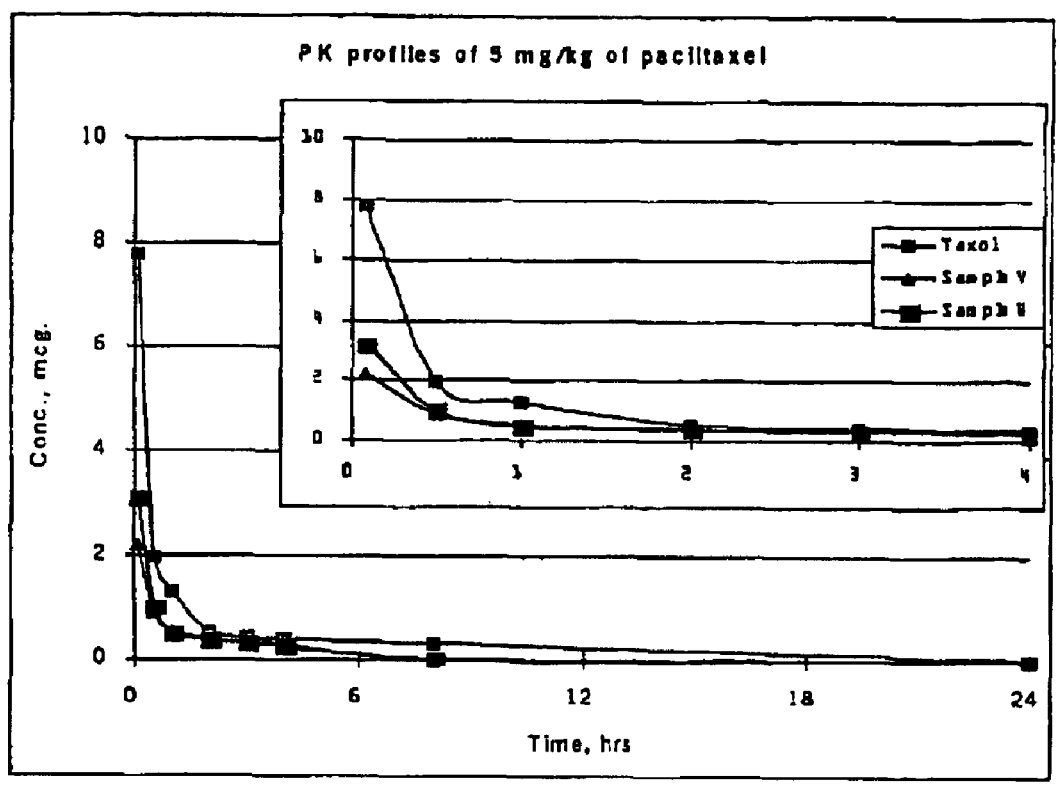
FIG. 1 is a pK profile comparison of 1) commercially available TAXOL® (Bristol-Myers Squibb Company), 2) Formulation V, and 3) Formulation W, in each case, upon adminstration of a 5 mg/kg bolus dose in male Sprague-Dawley rats.
Figure 2:
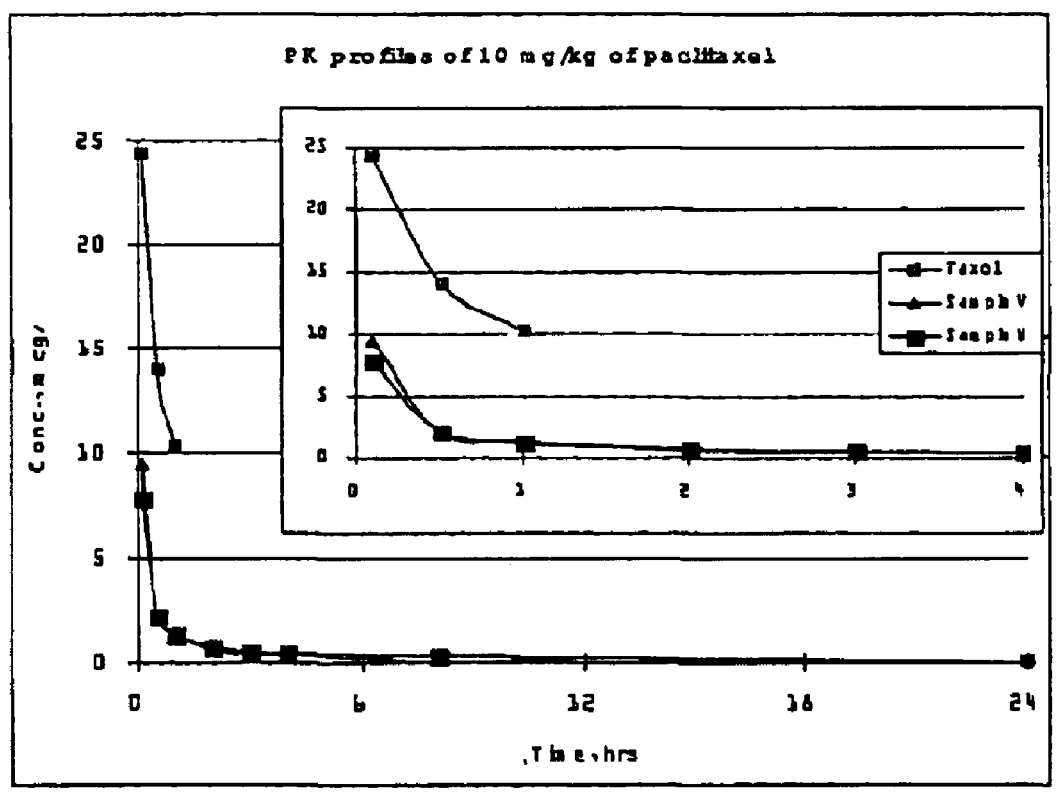
FIG. 2 is a pK profile comparison of 1) commercially available TAXOL®2) Formulation V, and 3) Formulation W, in each case, upon adminstration of a 10 mg/kg bolus dose in male Sprague-Dawley rats.
Figure 3:
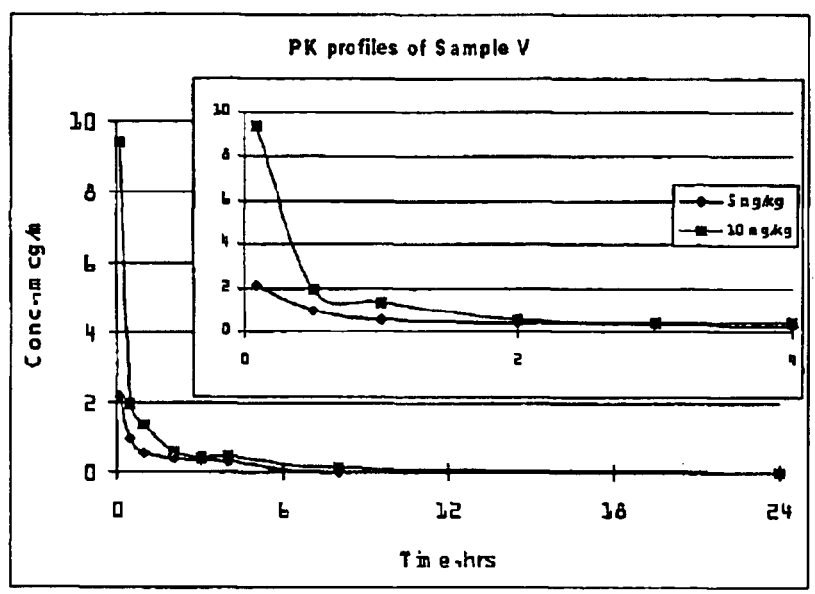
FIG. 3 is a pK profile comparison of 1) Formulation V upon adminstration of a 5 mg/kg bolus dose, and 2) Formulation V upon adminstration of a 10 mg/kg bolus dose, in male Sprague-Dawley rats.
Figure 4:
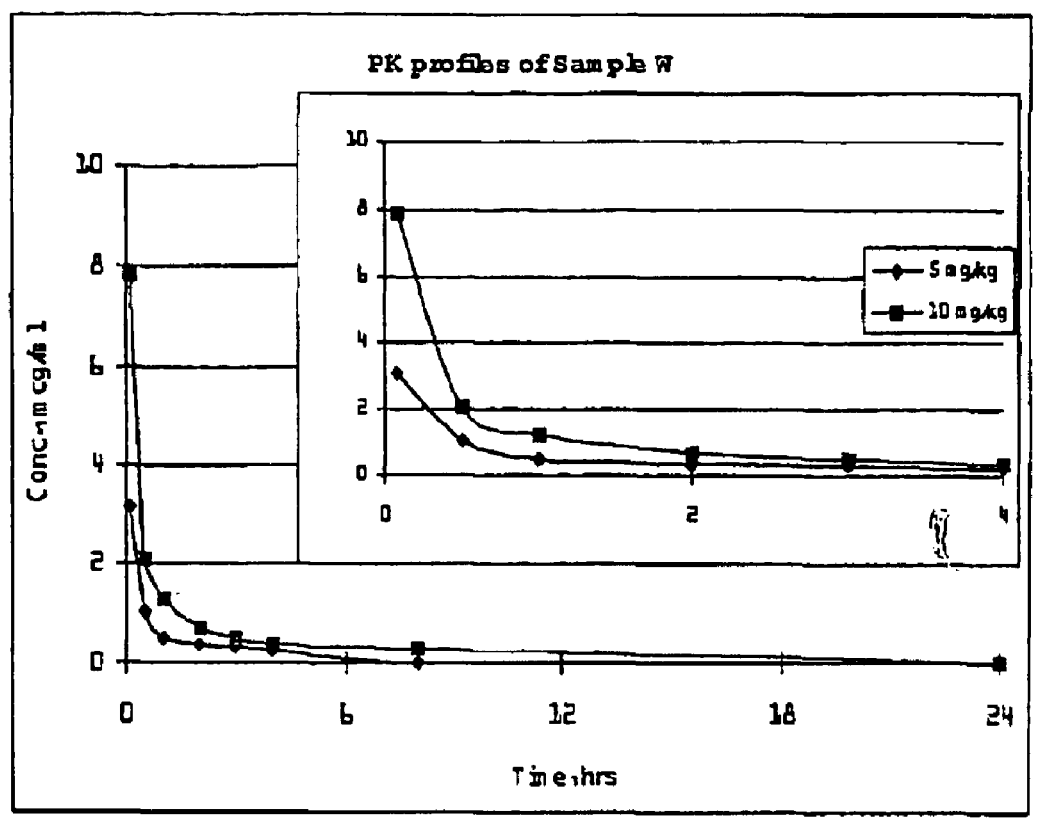

FIG. 4 is a pK profile comparison of 1) Formulation W upon adminstration of a 5 mg/kg bolus dose, and 2) Formulation W upon adminstration of a 10 mg/kg bolus dose, in male Sprague-Dawley 3.2 DEFINITIONS The term "mammal" as used herein, encompasses any mammal. Preferably a mammal is in need of a formulation of the invention. Examples of mammals include, but are not limited to, cows, horses, sheep, pigs, cats, dogs, mice, rats, rabbits, guinea pigs, monkeys, etc., more preferably, a human.

As referred to herein, derivatives and analogs of paclitaxel include, but are not limited to, docetaxel and compounds having the general formula I below and stereoisomers and pharmaceutically acceptable salts thereof:

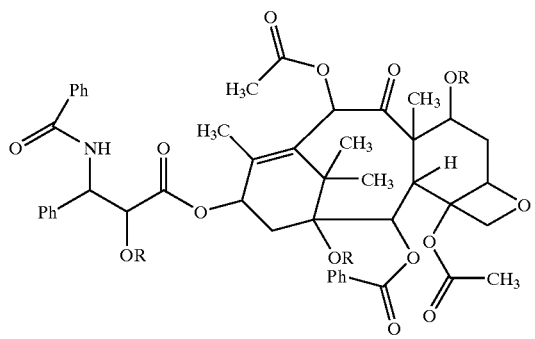

I wherein, each occurrence of R is independently H, $(C_1-C_6)$ alkyl, aryl, $C(O)(C_1-C_6)$alkyl, or C(O)aryl. Preferably, $(C_1-C_6)$alkyl is methyl and aryl is phenyl. Such derivatives are well known in the art. For example, paclitaxel derivatives encompassed by formula I are disclosed in U.S. Pat. Nos. 5,399,726; 5,654,447; 6,066,747; 5,338,872; 6,107,332; 5,703,117; 5,714,512; 5,580,899; 6,118,011; 5,470,866; 5,319,112; and 6,136,961.

As used herein, "paclitaxel solubilizer" means one or a mixture of substances that has a high propensity to solubilize paclitaxel in an aqueous medium. Preferably, a paclitaxel solubilizer, when included in an aqueous paclitaxel medium, can dissolve the paclitaxel at room temperature to a concentration of at least about 1.2 mg/ml water. A "paclitaxel solubilizer of the invention" refers to PEG-Vitamin Es, quaternary ammonium salts, PEG-monoacid fatty esters, polysorbates, and PEG-fatty alcohols or combinations thereof. It is to be understood that a "paclitaxel solubilizer" can be used to solubilize, distribute, and administer drugs generally, for example, the paclitaxel solubilizers of the invention can be used to solubilize, distribute, and administer, but not limited to, other cancer and cancer-related pharmaceuticals, such as cisplatin, carboplatin, epirubicin, leuprolide, bicalutamide, goserelin implant, irinotecan, gemcitabine, and sargramostim; cardiovascular drugs; such as amlodipine besylate, enalapril maleate, losartan potassium lisinopril, irbesartan, nifedipine, diltiazem, clopidogrel, digoxin, abciximab, furosemide, amiodarone, beraprost, and tocopheryl; anti-infective agents, such as amoxicillin, clavulanate, ciprofloxacin, azithromycin, itraconazole, acyclovir fluconazole, terbinafine, erythromycin, and sulfisoxazole acetyl; psychotherapeutic agents, such as fluoxetine, paroxetine, sertaline, vanlafaxine, bupropion, olanzapine, alprazolam, methylphenidate, fluvoxamine, and ergoloid; gastrointestinal medicaments, such as omeprazole, lansoprazole, ranitidine, famotidine, ondansetron, granisetron, sulfasalazine, and infliximab; respiratory therapies, such as loratadine, fexofenadine, cetirizine, fluticasone, salmeterol xinafoate, and budesonide; cholesterol reducers, such as simvastatin, atorvastatin calcium, pravastatin, lovastatin, bezafibrate, ciprofibrate, and gemfibrozil; blood modifiers, such as epoetin alpha, enoxaparin, and antihemophilic factor; antiarthritic agents, such as celecoxib, diclofenac sodium, nabumetone, misoprostol, and rofecoxib; AIDS and AIDS-related drugs, such as lamivudine, zidovudine, indinavir, stavudine, and lamivudine; diabetes and diabetes-related therapies, such as metformin, troglitazone, and acarbose; biologicals, such as hepatitis vaccines; Hormones, such as estradiol; immunosuppressive agents, such as cyclosporine, mycophenolate mofetil, and methylprednisolone; analgesics, such as tramadol, fentanyl, metamizole, ketoprofen, morphine, lysine acetylsalicylate, ketorolac tromethamine, morphine, loxoprofen sodium, and ibuprofen; dermatological products, such as isotretinoin and clindamycin; anesthetics, such as propofol, midazolam, and lidocaine; migraine therapies, such as sumatriptan succinate, zolmitriptan, and rizatriptan; sedatives and hypnotics, such as, zolpidem, triazolam, and hycosine butylbromide; multiple sclerosis agents, such as interferon beta-1a, interferon beta-1a, and glatiramer; osteoporosis agents, such as vitamin $k_2$; cystic fibrosis agents, such as dornase alpha and tobramycin; Alzheimer's disease therapies, such as dolasetron and donepezil; and imaging agents, such as iohexol, technetium Tc99m sestamibi, iomeprol, gadodiamide, ioversol, and ioprornide; or pharmaceutically acceptable salts thereof.

The term "active" refers to a pharmaceutical, more specifically to paclitaxel, derivatives, and pharmaceutically acceptable salts thereof.

The term "cremophor" means PEG-35 caster oil (commercially available from BASF, Washington, N.J., under the trade name Cremophor® EL).

As used herein, the phrase "formulations of the invention" refers to a specific composition or combination of ingredients (i.e., one or more paclitaxel solubilizer(s) and any other excipients, diluents, or carriers) useful for administering, delivering, or distributing paclitaxel, a derivative, or salt thereof. A "formulations of the invention" may or may not include an active. Preferably, the formulations of the invention are suitable for reconstitution or dissolution in an aqueous medium to a particulate-free, injectable solution. It is also preferable that formulations of the invention are sterile. A formulation of the invention can be in the form of a solid, liquid, semisolid, gel, suspension, emulsion, or a solution. A solution includes both aqueous and organic solvent solutions and liquid concentrates thereof.

As used herein, a "liquid concentrate" means a solution of active and one or more paclitaxel solubilizers of the invention, preferably in an organic solvent, such as ethanol, that is to be diluted with an aqueous medium prior to administration. A liquid concentrate can include various amounts of water but is preferably substantially anhydrous.

Solids include any solid form, such as a powder, a compressed pharmaceutical dosage form, or a lyophilized solid. In one embodiment, formulations of the invention if solid or other than liquid, are suitable for reconstitution into an injectable, particulate-free, preferably sterile formulation, such as an aqueous medium.

An "aqueous medium" will comprise at least water. Preferably, an aqueous medium is sterile and suitable for use as a carrier of an active for administration to a mammal. Examples of preferred aqueous mediums include, but are not limited to, water; saline solution; Ringer's solution; and solutions of water-miscible substance, such as dextrose and other electrolytes. Other aqueous mediums suitable for parenteral administration of actives are listed in *Remington: the Science and Practice of Pharmacy*, Alfonso R. Gennaro ed., Mack Publishing Co. Easton, Pa., 19th ed., 1995, Chapter 87; incorporated herein by reference. Preferably, the aqueous medium does not affect the ability of the paclitaxel solubilizer of the invention to solubilize paclitaxel, derivatives, or salts thereof.

The phrase "pharmaceutically acceptable salt(s)", as used herein, means those salts of paclitaxel derivatives that retain the biological effectiveness and properties of the free acids or free bases and that are not otherwise unacceptable for pharmaceutical use. Pharmaceutically acceptable salts of paclitaxel derivatives include salts of acidic or basic groups which may be present in the paclitaxel derivatives. Derivatives of paclitaxel that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as chloride, bromide, iodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate; saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Derivatives of paclitaxel that include an amino moiety can also form pharmaceutically acceptable salts with various amino acids, in addition to the acids mentioned above. Derivatives of paclitaxel that are acidic in nature are capable of forming a wide variety of salts with various inorganic and organic bases. Suitable base salts are formed from bases that donate cations to form non-toxic salts, suitable cations include, but are not limited to, sodium, aluminum, calcium, lithium, magnesium, potassium, zinc and diethanolamine salts. For a review on pharmaceutically acceptable salts see Berge et al., *J. Pharm. Sci.*, 66, 1–19 (1977), incorporated herein by reference.

As used herein, the term "excipient" means the substances used to formulate actives into pharmaceutical formulations; in a preferred embodiment, an excipient does not lower or interfere with the primary therapeutic effect of the active. Preferably, an excipient is therapeutically inert. The term "excipient" encompasses carriers, diluents, vehicles, solubilizers, stabilizers, and binders. Excipients can also be those substances present in a pharmaceutical formulation as an indirect result of the manufacturing process. Preferably, excipients are approved for or considered to be safe for human and animal administration, i.e., GRAS substances (generally regarded as safe). GRAS substances are listed by the Food and Drug administration in the Code of Federal Regulations (CFR) at 21 CFR 182 and 21 CFR 184, incorporated herein by reference.

As used herein, the phrase "array" means a plurality of samples associated under a common experiment, wherein each of the samples comprises at least paclitaxel, a derivative, or salt thereof (i.e., an active) and a formulation component. The array is designed to provide a data set, analysis of which allows detection or measurement of interactions (including lack of interactions) between the active and the formulation component. Samples in the array differ from other samples in the array with respect to at least one of:

(i) the identity of the formulation component, or (ii) the ratio of the active to the formulation component.

According to the invention, the ratio of the active to the formulation component will differ between samples when such ratio is intentionally varied to induce a measurable change in the sample's properties.

As used herein, the term "property" means a physical or chemical characteristic of a sample. Preferred properties are those that relate to the efficacy, safety, stability, or utility of formulations before or after administration. Properties include physical properties, for example, but not limited to, rheology, friability, stability, solubility, dissolution, and permeability, preferably, solubility. The term "property" also includes mechanical properties, for example, but not limited to, compressibility, compactability, and flow characteristics.

An array can comprise 24, 36, 48, 96, or more samples, preferably 1000 or more samples, more preferably, 10,000 or more samples. An array is typically comprises one or more sub-arrays. For example, a sub-array can be a 96-well plate of sample wells.

As used herein, the term "sample" means a mixture of paclitaxel, a derivative, or salt thereof (i.e., an active) and one or more formulation components. The term "sample" encompasses duplicates, triplicates, etc. of the same sample used as controls in an array. In other words, multiples of the same sample in an array, for control purposes, are considered one sample for the purposes of the invention. Preferably a sample comprises 2 or more formulation components, more preferably, 3 or more formulation components. A sample can be present in any container or holder or in or on any material or surface, the only requirement is that the samples be located at separate sites. Preferably, samples are contained in sample wells, for example, a 24, 36, 48, or 96 well plates (or filter plates) of volume 250 ul available from Millipore, Bedford, Mass.

As used herein, the phrase "formulation component" means any substance in addition to the active in a sample. Preferably, a formulation component is therapeutically inactive. Examples of suitable formulation components include, but are not limited to, excipients, solvents, diluents, stabilizers, and combinations thereof.

As used herein, the term "alkyl group" means a saturated, monovalent, unbranched or branched hydrocarbon chain. Examples of alkyl groups include, but are not limited to, $(C_1-C_{25})$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, and longer alkyl groups, such as heptyl, and octyl, nonyl, decyl, undecyl, dodecyl, tridecyl, tetradecyl, pentadecyl, hexadecyl, heptadecyl, octadecyl, nonadecyl, icosanyl, heniconsanyl, docosanyl, tricosanyl, tetracosanyl, and pentacosanyl. An alkyl group can be unsubstituted or substituted with one or more suitable substituents.

An "alkenyl group" means a monovalent, unbranched or branched hydrocarbon chain having one or more double bonds therein. The double bond of an alkenyl group can be unconjugated or conjugated to another unsaturated group. Suitable alkenyl groups include, but are not limited to $(C_2-C_{25})$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, nonenyl, decenyl, undecenyl, dodecenyl, tridecenyl, tetradecenyl, pentadecenyl, hexadecenyl, heptadecenyl, octadecenyl, nonadecenyl, icosanenyl, heniconsanenyl, docosanenyl, tricosanenyl, tetracosanenyl, and pentacosanenyl. An alkenyl group can be unsubstituted or substituted with one or more suitable substituents.

An "alkynyl group" means monovalent, unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_{25})$alkynyl groups, such as ethynyl, propynyl, butynyl, pentynyl, hexynyl, methylpropynyl, 4-methyl-1-butynyl, 4-propyl-2-pentynyl, 4-butyl-2-hexynyl, nonynyl, decynyl, undecynyl, dodecynyl, tridecynyl, tetradecynyl, pentadecynyl, hexadecenyl, heptadecynyl, octadecynyl, nonadecynyl, icosanynyl, heniconsanynyl, docosanynyl, tricosanynyl, tetracosanynyl, and pentacosanynyl. An alkynyl group can be unsubstituted or substituted with one or more suitable substituents.

An "aryl group" means a monocyclic or polycyclic-aromatic ring comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more suitable substituents. Preferably, the aryl group is a monocyclic ring, wherein the ring comprises 6 carbon atoms, referred to herein as "$(C_6)$aryl".

A "cycloalkyl group" means a monocyclic or polycyclic saturated ring comprising carbon and hydrogen atoms and having no carbon-carbon multiple bonds. Examples of cycloalkyl groups include, but are not limited to, ($C_3$–$C_7$) cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted by one or more suitable substituents. Preferably, the cycloalkyl group is a monocyclic ring or bicyclic ring.

The term "alkoxy group" means an —O-alkyl group, wherein alkyl is as defined above. An alkoxy group can be unsubstituted or substituted with one or more suitable substituents. Preferably, the alkyl chain of an alkoxy group is from 1 to 25 carbon atoms in length, referred to herein as "—($C_1$–$C_{25}$)alkoxy".

The term "aryloxy group" means an —O-aryl group, wherein aryl is as defined above. An aryloxy group can be unsubstituted or substituted with one or more suitable substituents. Preferably, the aryl ring of an aryloxy group is a monocyclic ring, wherein the ring comprises 6 carbon atoms, referred to herein as "($C_6$)aryloxy".

The term "benzyl" means —$CH_2$-phenyl.

The term "phenyl" means —$C_6H_5$. A phenyl group can be unsubstituted or substituted with one or more suitable substituents.

A "carbonyl" group is a divalent group of the formula —C(O)—.

An "alkoxycarbonyl" group means a monovalent group of the formula —C(O)-alkoxy. Preferably, the hydrocarbon chain of an alkoxycarbonyl group is from 1 to 25 carbon atoms in length.

As used herein, "halogen" means fluorine, chlorine, bromine, or iodine. Correspondingly, the meaning of the terms "halo" and "Hal"encompass fluoro, chloro, bromo, and iodo.

As used herein, a "suitable substituent" means a group that does not nullify the synthetic or pharmaceutical utility of the active or the paclitaxel solubilizer of the invention. Examples of suitable substituents include, but are not limited to: ($C_1$–$C_8$)alkyl; ($C_1$–$C_8$)alkenyl; ($C_1$–$C_8$)alkynyl; ($C_6$) aryl; ($C_2$–$C_5$)heteroaryl; ($C_3$–$C_7$)cycloalkyl; ($C_1$–$C_8$) alkoxy; ($C_6$)aryloxy; CN; OH; oxo; halo, $CO_2$H; $NH_2$; NH(($C_1$–$C_8$)alkyl); N(($C_1$–$C_8$)alkyl)$_2$; NH(($C_6$)aryl); N(($C_6$)aryl)$_2$; CHO; CO(($C_1$–$C_8$)alkyl); CO($C_6$)aryl); $CO_2$ (($C_1$–$C_8$)alkyl); and $CO_2$(($C_6$)aryl). One of skill in art can readily choose a suitable substituent based on the stability and pharmacological and synthetic activity of the paclitaxel solubilizer of the invention.

As used herein, a "PEG-vitamin E" means a compound of the formula:

include tocophereth-5, tocophereth-10, tocophereth-12, tocophereth-18, and tocophereth-50. In such tocophereths, x is 0 and the average ethoxylation value is 5, 10, 12, 18, and 50 respectively. PEG-vitamin Es are available commercially, for example, from Eastman Chemical Co., Kingsport, Tenn. and Pacific Corporation, Seoul, Korea.

As used herein, a quaternary ammonium salt means a compound of the general formula:

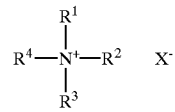

wherein $R^1$, $R^2$, $R^3$, $R^4$ are independently selected from the group consisting of ($C_1$–$C_{25}$)alkyl, aryl, ($C_1$–$C_{25}$)alkylaryl, ($C_2$–$C_{25}$)alkenyl, ($C_2$–$C_{25}$)alkynyl, ($C_2$–$C_{25}$)alkenylaryl, ($C_2$–$C_{25}$)alkynylaryl, phenyl, and benzyl.

The group X is a suitable anion, for example, but not limited to, halide, acetate, benzenesulfonate, benzoate, bicarbonate, bitartrate, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydroxynaphthoate, isethionate, lactate, lactobionate, malate, maleate, mandelate, mesylate, methylbromide, methylnitrate, methylsulfate, muscate, napsylate, nitrate, pamoate (embonate), panthothenate, phosphate/diphosphate, polygalacturonate, salicylate, stearate, subacetate, succinate, sulfate, tannate, tartrate, teoclate, and triethiodide. Preferred quaternary ammonium salts include, but are not limited to, benzethonium chloride, benzalkonium chloride, and cetrimide.

As used herein, the term "polyethylene glycol of a fatty alcohol (PEG-fatty alcohol)" means a compound of the formula:

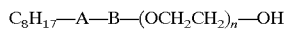

wherein n has an average value of about 1 to about 75; the variable "A" represents the optional presence of one or more carbon-carbon double bonds and the variable "B" represents ($C_1$–$C_{15}$)alkyl. Preferred PEG-fatty alcohols are octoxynols, oleths, and laureths. As used herein, an "octoxynol" is a compound of the formula:

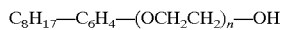

wherein n is an integer having an average value of about 1 to about 75, preferably, n has an average value of 1, 3, 5, 7,

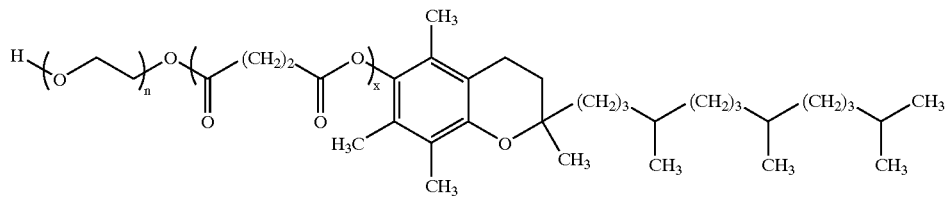

wherein the variable x is 0 or 1 and the variable n is about 1 to about 20,000, preferably, from about 3 to about 1000. Preferably, the PEG-vitamin E is α-tocopheryl polyethylene glycol 1000 succinate, referred to herein as tocophersolan (sold by Eastman Chemical Co. under the trade name vitamin E TPGS NF). In tocophersolan, x is 1 and n has an average value of 22. Other preferred PEG-vitamin Es, 8, 9, 10, 11, 12, 13, 16, 20, 25, 30, 33, 40, or 70, more preferably, n has an average value of about 7 to 12, more preferably about 9. Preferred octoxynols include octoxynol-9 (Triton® X-100). Octoxynols are commercially available, for example, from Rhône-Poulenc, Shelton, Conn. under the trade name TRITON.

As used herein, an "oleth" is a compound of the formula:

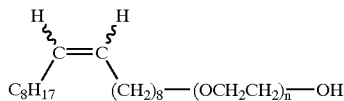

wherein n is an integer having an average value of about 1 to about 55, preferably, n has an average value of 2, 3, 4, 5, 6, 7, 8, 9, 10, 11, 12, 15, 16, 20, 25, 40, 44, or 50, more preferably, n has an average value of about 7 to 12, more preferably about 9. Oleths are commercially available, for example, from ICI Surfactants, Wilmington, Del. under the trade name BRIJ or from Heterene, Inc., Paterson, N.J. under the trade name HETOXOL.

As used herein, a "laureth" is a compound of the formula:

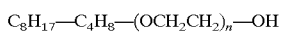

wherein n is an integer having an average value of about 1 to about 55, preferably, n has an average value of 1, 2, 3, 4, 5, 6, 7, 8, 9, 10, 11, 12, 15, 16, 20, 23, 25, 30, or 40 more preferably, n has an average value of about 7 to 12, more preferably about 23 (i.e., laureth-23 also known as BRIJ 35, ICI Surfactants). Laureths are commercially available, for example, from ICI Surfactants, Wilmington, Del. under the trade name BRIJ or from Rhône-Poulenc, Shelton, Conn. under the trade name RHODASURF.

As used herein, the term "polysorbate" means a compound of the general formula:

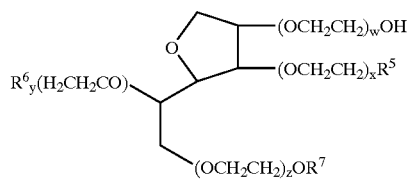

wherein the sum of W+X+Y+Z is an integer having an average value of about 5, 4, or 20; $R^5$, $R^6$, and $R^7$ are independently H,

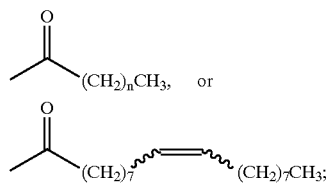

and n is an integer ranging from 8 to 20. Preferred polysorbates are polysorbate 20, 21, 40, 60, 61, 65, 80, 81, 85, more preferably polysorbate 20 or polysorbate 80. Polysorbates are available commercially under the trade name TWEEN from Rhône-Poulenc, Shelton, Conn.

As used herein, the term "polyethyleneglycol monoacid fatty ester" (PEG-monoacid fatty ester) means a compound of the general formula:

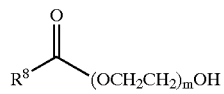

where $R^8$ is $(C_1–C_{25})$alkenyl, $(C_2–C_{25})$alkenyl, or $(C_2–C_{25})$ alkynyl, in substantially pure form. As used herein, "substantially pure form" means that at least about 85% of polyethyleneglycol monoacid fatty ester is a single polyethyleneglycol monoacid fatty ester, preferably about 95%. The variable m is an integer having an average value of from 2 to 200, preferably, 6 to 150, more preferably, 10 to 50. Preferably, $R^8$ is $(C_8–C_{20})$ or $(C_8–C_{20})$alkenyl. Preferably, $R^8(CO)O$ is laurate, oleate, or stearate. Preferred PEG-monoacid fatty esters include, but are not limited to, PEG-20 monolaurate, PEG-20 monooleate, and PEG-20 monostearate.

As used herein, the term "polyethyleneglycol-glyceryl fatty ester" (PEG-glyceryl fatty ester) means a compound of the general formula:
where $R^9$ is independently OH, $OCOR^8$, $(OCH_2CH_2)_mOH$, or $(OCH_2CH_2)_mOCOR^8$, wherein:

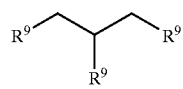

(a) at least one of $R^9$ is $OCOR^8$ and one of $R^9$ is $(OCH_2CH_2)_mOH$; or (b) at least one of $R^9$ is $(OCH_2CH_2)_mOCOR^8$.

$R^8$ is $(C_1–C_{25})$alkyl, $(C_2–C_{25})$alkenyl, or $(C_2–C_{25})$alkynyl. And The variable m is an integer having an average value of from 2 to 200, preferably, 6 to 150, more preferably, 10 to 50. Preferably, $R^8$ is $(C_8–C_{20})$ or $(C_8–C_{20})$alkenyl. Preferably $R^8(CO)O$ is laurate, oleate, or stearate.

A subclass of PEG-glyceryl fatty esters has the formula:

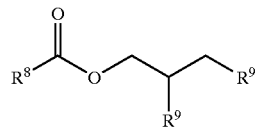

where $R^8$ is $(C_1–C_{25})$alkyl, $(C_2–C_{25})$alkenyl, or $(C_2–C_{25})$ alkynyl. And $R^9$ is independently OH, $OCOR^8$, $(OCH_2CH_2)_mOH$, or $(OCH_2CH_2)_mOCOR^8$, wherein at least one of $R^9$ is $(OCH_2CH_2)_mOH$ or $(OCH_2CH_2)_mOCOR^8$. The variable m is an integer having an average value of from 2 to 200, preferably, 6 to 150, more preferably, 10 to 50. Preferably, $R^8$ is $(C_8–C_{20})$ or $(C_8–C_{20})$alkenyl. Preferably $R^8(CO)O$ is laurate, oleate, or stearate.

A further subclass of PEG-glyceryl fatty esters has the formula:

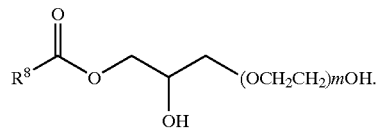

Wherein $R^8$ is defined as above. Preferred PEG-glyceryl fatty esters include, but are not limited to, PEG-20 glyceryl monooleate, PEG-20 glyceryl monostearate, and PEG-20 glyceryl monolaurate.

4. DETAILED DESCRIPTION OF THE INVENTION

The invention encompasses cremophor-free formulations comprising paclitaxel, derivatives, or pharmaceutically acceptable salts thereof and one or more paclitaxel solubilizers that are useful for use in mammals, particularly humans. Paclitaxel solubilizers of the invention include compounds falling within the classes of PEG-Vitamin Es; quaternary ammonium salts; PEG-monoacid fatty esters; PEG-glyceryl fatty esters; polysorbates; PEG-fatty alcohols. These formulations are advantageous in that they do not contain cremophor and thus avoid or reduce the toxicities and other disadvantages of cremophor formulations. The formulations of the invention also solubilize paclitaxel in aqueous medium and thus are particularly advantageous because paclitaxel is practically insoluble in water.

The formulations of the invention are useful for treating mammalian cancers and other medical conditions treatable by paclitaxel. By "treating" it is meant that the formulations are administered to inhibit or reduce the rate of cancer-cell proliferation in an effort to induce partial or total remission, for example, inhibiting cell division by promoting microtubule formation. For instance, the formulations of the invention are useful for treating solid tumors and blood-born tumors. Examples of cancers treatable or preventable by formulations of the invention include, but are not limited to, cancers of the lymph node; breast; cervix; uterus; gastrointestinal tract; lung; ovary; prostate; mouth; brain; head; neck; throat; testes; kidney; pancreas; bone; spleen; liver; bladder; skin; larynx; nasal passages; AIDS-related cancers, and cancers of the blood. The formulations can be used alone or in combination with other chemotherapeutics. The mode, dosage, and schedule of administration of paclitaxel, derivatives, and pharmaceutically acceptable salts thereof in human cancer patients have been extensively studied, see, e.g. 1989 *Ann. Int. Med.,* 111:273–279, incorporated herein by reference.

The invention encompasses single-unit dosage forms and multi-unit dosage forms of paclitaxel, derivatives, and pharmaceutically acceptable salts thereof in solid, liquid, semisolid, gel, suspension, emulsion, or solution form. In one embodiment, the invention relates to single-unit dosage and multi-unit dosage forms. In another embodiment, the invention relates to single-unit dosage and multi-unit dosage forms of liquid-concentrates, solids, semi-solids, and gels in concentrated form for further formulation (e.g. lyophilized solids and liquid concentrates for reconstitution prior to parenteral administration). Formulations of the invention in liquid-concentrate form are, preferably, in an organic solvent, such as ethanol or aqueous ethanol, that is to be diluted with an aqueous medium prior to administration.

Gennaro ed., Mack Publishing Co. Easton, Pa., 19th ed., 1995, Chapters 87 and 88; incorporated herein by reference. A comprehensive discussion on formulating solid forms, such as powders, tablets, pills, and capsules is presented in *Remington: the Science and Practice of Pharmacy,* Alfonso R. Gennaro ed., Mack Publishing Co. Easton, Pa., 19th ed., 1995, Chapters 91 and 92, incorporated herein by reference. A comprehensive discussion on formulating solutions, emulsions, and suspensions is presented in *Remington: the Science and Practice of Pharmacy,* Alfonso R. Gennaro ed., Mack Publishing Co. Easton, Pa., 19th ed., 1995, Chapter 86, incorporated herein by reference. Formulations of the invention in the form of gels and semisolids containing the active can be prepared according to well known methods. For instance, by mixing the active with the paclitaxel solubilizers of the invention, and any additional components or excipients in a standard V-blender. Preferably, for reconstitution, solids (e.g., lyophilized solids), liquid concentrates, semisolids, gels, suspensions, and emulsions, contain about 25 milligrams to about 2500 milligrams of active, more preferably, about 50 milligrams to about 500 milligrams.

The paclitaxel solubilizers of the invention are used in formulations of the invention in amounts that enhance the solubility of paclitaxel, derivatives, and pharmaceutically acceptable salts thereof in an aqueous medium. Armed with the present disclosure that specifies specific paclitaxel solubilizers and combinations thereof that enhance the aqueous solubility of paclitaxel, derivatives, and pharmaceutically acceptable salts thereof, one of skill in the art can readily determine suitable paclitaxel-solubilizer amounts by simple solubility experiments. For example, by mixing the paclitaxel solubilizer and the active, contacting the resulting mixture with an aqueous medium, filtering, and measuring the amount of dissolved active, for example, by spectrophotometry.

In one embodiment, the amount(s) of paclitaxel solubilizer in formulations of the invention can be expressed as a ratio relative to the amount of active. This is particularly useful when formulating a formulation of the invention in other than liquid form, e.g., solid, semisolid, gel, suspension, or emulsion, for example, a lyophilized solid. Preferred ratios of paclitaxel solubilizers to paclitaxel, derivatives, and pharmaceutically acceptable salts thereof are as follows:

| Excipient Class | Preferred ratio of paclitaxel solubilizer expressed as unit weight per unit weight of paclitaxel, derivative, or salt thereof | More preferred ratio of paclitaxel solubilizer expressed as unit weight per unit weight of paclitaxel, derivative, or salt thereof |
| --- | --- | --- |
| PEG-Vitamin Es | about 5 to about 200 | about 10 to about 100 |
| Quaternary ammonium salts | about 0.01 to about 1 | about 0.016 to about 0.3 |
| PEG-monoacid fatty esters | about 5 to about 200 | about 10 to about 100 |
| PEG-glyceryl fatty esters | about 5 to about 200 | about 10 to about 100 |
| Polysorbates | about 5 to about 200 | about 10 to about 100 |
| PEG-fatty alcohols | about 5 to about 200 | about 10 to about 100 |

Preferably, the formulations are easy to handle, stable for storage and shipment, and inexpensive to manufacture compared to previous paclitaxel formulations. Preferably, the formulations of the invention are sterile.

The formulations of the invention can be prepared by combining the actives, solubilizers of the invention, and other components using well-known pharmaceutical-formulation methods. Formulation of liquid dosage forms, such as for intravenous administration is described in *Remington: the Science and Practice of Pharmacy,* Alfonso R.

In another embodiment, the formulations of the invention comprise an aqueous medium. Preferably, such a formulation is suitable for parenteral administration. In this embodiment, the preferred concentration of paclitaxel, a derivative, or a salt thereof is from about 0.2 mg/ml to about 3 mg/ml, more preferably, about 0.3 mg/ml to about 1.2 mg/ml. Preferred concentrations of paclitaxel solubilizers for use with aqueous paclitaxel solutions of the invention are as follows:

| Excipient Class | Preferred concentrations of paclitaxel solubilizers in an aqueous medium (mg/ml) | More preferred concentrations of paclitaxel solubilizers in an aqueous medium (mg/ml) |
| --- | --- | --- |
| PEG-Vitamin Es | about 3 to about 120 | about 15 to about 100 |
| Quaternary ammonium salts | about 0.0048 to about 0.35 | about 0.001 to about 0.2 |
| PEG-monoacid fatty esters | about 3 to about 120 | about 15 to about 100 |
| PEG-glyceryl fatty esters | about 3 to about 120 | about 15 to about 100 |
| Polysorbates | about 3 to about 120 | about 15 to about 80 |
| PEG-fatty alcohols | about 3 to about 120 | about 15 to about 110 |

In another embodiment, the formulations of the invention are in liquid-concentrate form. Liquid concentrate meaning that the formulations are to be diluted prior to parenteral administration, preferably, diluted with an aqueous medium. Preferably, liquid concentrates of the invention have less than about 5% by weight water, more preferably, less than about 1%, even more preferably, liquid concentrates are substantially anhydrous. Preferably, the concentration of paclitaxel in liquid concentrates of the invention is from about 3 mg/ml to about 10 mg/ml, more preferably, about 6 mg/ml. Paclitaxel solubilizers of the invention can comprise about 0.1% to about 99% by weight of liquid-concentrate formulations of the invention. Preferably, liquid concentrates of the invention comprise about 20% to about 99% total solubilizer weight, e.g., about 20% to about 99% total weight of one or more of a PEG-vitamin E, a PEG-monoacid fatty ester, a PEG-glyceryl fatty ester, a polysorbate, or a PEG-fatty alcohol. Thus, preferably, in a liquid-concentrate formulations, when one paclitaxel solubilizer of the invention is used in combination with one or more other paclitaxel solubilizers of the invention, the total paclitaxel-solubilizer weight percent is from about 20% to about 99%. Preferably, when combinations of paclitaxel solubilizers are used in liquid-concentrate formulations, each individual paclitaxel solubilizer (excluding the class of quaternary ammonium salts) represents at least about 5% by weight of the total paclitaxel-solubilizer weight. When a quaternary ammonium salt is included in a liquid-concentrate formulation of the invention, the preferred concentration is about 0.005 mg/ml to about 5 mg/ml.

A few preferred liquid concentrate formulations of the invention (i.e., formulations 1–13) are shown below.

Formulation 1

| Component | Weight % range | Preferred weight % range |
| --- | --- | --- |
| Paclitaxel | 0.1% to 1% | 0.1% to 1% |
| *PEG-400 | 0.1% to 99% | 2.5% to 92.5% |
| *Polysorbate 80 | 0.1% to 99% | 2.5% to 92.5% |
| Ethanol | 0% to 49% | 5% to 59% |
| Benzethonium chloride | 0% to 0.2% | 0% to 0.2% |
| Citric acid | 0.01% to 1% | 0.01% to 1% |

*The combination of PEG-400 and Polysorbate 80 comprises at least about 40% by weight of the formulation.

Formulation 2

| Component | Weight % range | Preferred weight % range |
| --- | --- | --- |
| Paclitaxel | 0.1% to 1% | 0.1% to 1% |
| *PEG-20 glyceryl monooleate | 0.1% to 99% | 2% to 93% |
| Ethanol | 0% to 59% | 5% to 69% |
| *Polysorbate 80 | 0.1% to 99% | 2% to 93% |
| Benzethonium chloride | 0% to 0.2% | 0% to 0.2% |
| Citric acid | 0.01% to 1% | 0.01% to 1% |

*The combination of PEG-20 glyceryl monooleate and Polysorbate 80 comprises at least about 30% by weight of the formulation.

Formulation 3

| Component | Weight % range | Preferred weight % range |
| --- | --- | --- |
| Paclitaxel | 0.1% to 1% | 0.1% to 1% |
| *PEG-20 glyceryl monooleate | 0.1% to 99% | 1% to 94% |
| Ethanol | 0% to 79% | 5% to 79% |
| *Vitamin E TPGS | 0.1% to 99% | 1% to 94% |
| Benzethonium chloride | 0% to 0.2% | 0% to 0.2% |
| Citric acid | 0.01% to 1% | 0.01% to 1% |

*The combination of PEG-20 glyceryl monooleate and Vitamin E TPGS comprises at least about 20% by weight of the formulation.

Formulation 4

| Component | Weight % range | Preferred weight % range |
| --- | --- | --- |
| Paclitaxel | 0.1% to 1% | 0.1% to 1% |
| *PEG-20 glyceryl monooleate | 0.1% to 99% | 2% to 93% |
| Ethanol | 0% to 59% | 5% to 69% |
| *PEG-20 monolaurate | 0.1% to 99% | 2% to 93% |
| Benzethonium chloride | 0% to 0.2% | 0% to 0.2% |
| Citric acid | 0.01% to 1% | 0.01% to 1% |

*The combination of PEG-20 glyceryl monooleate and PEG-20 monolaurate comprises at least about 30% by weight of the formulation.

Formulation 5

| Component | Weight % range | Preferred weight % range |
|---|---|---|
| Paclitaxel | 0.1% to 1% | 0.1% to 1% |
| *PEG-20 glyceryl monooleate | 0.1% to 99% | 2% to 93% |
| Ethanol | 0% to 59% | 5% to 69% |
| *Polysorbate 20 | 0.1% to 99% | 2% to 93% |
| Benzethonium chloride | 0% to 0.2% | 0% to 0.2% |
| Citric acid | 0.01% to 1% | 0.01% to 1% |

*The combination of PEG-20 glyceryl monooleate and Polysorbate 20 comprises at least about 30% by weight of the formulation.

Formulation 6

| Component | Weight % range | Preferred weight % range |
|---|---|---|
| Paclitaxel | 0.1% to 1% | 0.1% to 1% |
| *PEG-20 glyceryl monooleate | 0.1% to 99% | 2% to 93% |
| Ethanol | 0% to 59% | 5% to 69% |
| *PEG-20 monooleate | 0.1% to 99% | 2% to 93% |
| Benzethonium chloride | 0% to 0.2% | 0% to 0.2% |
| Citric acid | 0.01% to 1% | 0.01% to 1% |

*The combination of PEG-20 glyceryl monooleate and PEG-20 monooleate comprises at least about 30% by weight of the formulation.

Formulation 7

| Component | Weight % range | Preferred weight % range |
|---|---|---|
| Paclitaxel | 0.1% to 1% | 0.1% to 1% |
| Ethanol | 0% to 79% | 5% to 79% |
| Vitamin E TPGS | 20% to 99% | 20% to 94% |
| Benzethonium chloride | 0% to 0.2% | 0% to 0.2% |
| Citric acid | 0.01% to 1% | 0.01% to 1% |

Formulation 8

| Component | Weight % range | Preferred weight % range |
|---|---|---|
| Paclitaxel | 0.1% to 1% | 0.1% to 1% |
| Ethanol | 0% to 80% | 5% to 80% |
| *Vitamin E TPGS | 0.1% to 99% | 1% to 94% |
| *PEG-400 | 0.1% to 99% | 1% to 94% |
| Benzethonium chloride | 0% to 0.2% | 0% to 0.2% |
| Citric acid | 0.01% to 1% | 0.01% to 1% |

*The combination of Vitamin E TPGS and PEG-400 comprises at least about 20% by weight of the formulation.

Formulation 9

| Component | Weight % range | Preferred weight % range |
|---|---|---|
| Paclitaxel | 0.1% to 1% | 0.1% to 1% |
| Ethanol | 0% to 80% | 5% to 80% |
| *Vitamin E TPGS | 0.1% to 99% | 1% to 94% |
| *PEG-20 monooleate | 0.1% to 99% | 1% to 94% |
| Benzethonium chloride | 0% to 0.2% | 0% to 0.2% |
| Citric acid | 0.01% to 1% | 0.01% to 1% |

*The combination of Vitamin E TPGS and PEG-20 monooleate comprises at least about 20% by weight of the formulation.

Formulation 10

| Component | Weight % range | Preferred weight % range |
|---|---|---|
| Paclitaxel | 0.1% to 1% | 0.1% to 1% |
| Ethanol | 0% to 80% | 5% to 80% |
| *Vitamin E TPGS | 0.1% to 99% | 1% to 94% |
| *Polysorbate 80 | 0.1% to 99% | 1% to 94% |
| Benzethonium chloride | 0% to 0.2% | 0% to 0.2% |
| Citric acid | 0.01% to 1% | 0.01% to 1% |

*The combination of Vitamin E TPGS and Polysorbate 80 comprises at least about 20% by weight of the formulation.

Formulation 11

| Component | Weight % range | Preferred weight % range |
|---|---|---|
| Paclitaxel | 0.1% to 1% | 0.1% to 1% |
| Ethanol | 0% to 80% | 5% to 80% |
| *Vitamin E TPGS | 0.1% to 99% | 1% to 94% |
| *Polysorbate 20 | 0.1% to 99% | 1% to 94% |
| Benzethonium chloride | 0% to 0.2% | 0% to 0.2% |
| Citric acid | 0.01% to 1% | 0.01% to 1% |

*The combination of Vitamin E TPGS and Polysorbate 20 comprises at least about 20% by weight of the formulation.

Formulation 12

| Component | Weight % range | Preferred weight % range |
|---|---|---|
| Paclitaxel | 0.1% to 1% | 0.1% to 1% |
| Ethanol | 0% to 80% | 5% to 80% |
| *Vitamin E TPGS | 0.1% to 99% | 1% to 94% |
| *PEG-20 monolaurate | 0.1% to 99% | 1% to 94% |
| Benzethonium chloride | 0% to 0.2% | 0% to 0.2% |
| Citric acid | 0.01% to 1% | 0.01% to 1% |

*The combination of Vitamin E TPGS and PEG-20 monolaurate comprises at least about 20% by weight of the formulation.

Formulation 13

| Component | Weight % range | Preferred weight % range |
|---|---|---|
| Paclitaxel | 0.1% to 1% | 0.1% to 1% |
| Ethanol | 0% to 70% | 5% to 70% |
| *Polysorbate 80 | 0.1% to 99% | 1% to 94% |
| *PEG-20 monooleate | 0.1% to 99% | 1% to 94% |
| Benzethonium chloride | 0% to 0.2% | 0% to 0.2% |
| Citric acid | 0.01% to 1% | 0.01% to 1% |

*The combination of Polysorbate 80 and PEG-20 monooleate comprises at least about 30% by weight of the formulation.

The formulations of the invention can include additional pharmaceutically acceptable excipients. Preferred additional excipients do not affect the ability of the paclitaxel solubilizers of the invention to solubilize paclitaxel. Preferred additional excipients for intravenous administration are water, aqueous vehicles such as saline, Ringer's solution, or dextrose solution. Other examples of suitable excipients, such as binders and fillers are listed in *Remington: the Science and Practice of Pharmacy*, 18th Edition, ed. Alfonso Gennaro, Mack Publishing Co. Easton, Pa., 1995 and Handbook of Pharmaceutical Excipients, 3rd Edition, ed. Arthur H. Kibbe, American Pharmaceutical Association, Washington D.C. 2000. Whatever excipient is incorporated into the present formulations, preferably, that excipient is sterile when added, or sterilized during the same process that sterilizes the formulation.

Administration of formulations of the invention can be systemic or local. In most instances, administration to a mammal will result in systemic release of the active (i.e., into the bloodstream). Methods of administration include enteral routes, such as oral administration; topical routes, such as local, transdermal and intradermal administration; and parenteral routes, such as intravenous injection. Preferably, the formulations of the invention are administered intravenously.

Typically, formulation of the invention for parenteral administration are solutions in sterile isotonic aqueous vehicles, such as water, saline, Ringer's solution, or dextrose solution. Formulations for intravenous administration may optionally include a local anesthetic such as lignocaine to ease pain at the site of the injection. For parenteral administration, the formulations of the invention can be supplied as a sterile, dry lyophilized powder or a water-free liquid concentrate in a hermetically sealed container, such as an ampoule or an i.v. bag, the container indicating the quantity of active. Such a powder or concentrate is then diluted with an appropriate aqueous medium prior to administration. An ampoule of sterile water, saline solution, or other appropriate aqueous medium can be provided with the powder or concentrate in a separate container to dilute the active prior to administration. Alternatively, the formulations can be supplied in pre-mixed form, ready for administration.

A further embodiment of the present invention includes a sterilization step. The sterilization may be carried out in several ways, e.g., by using a bacteriological filter, by incorporating sterilizing agents into the composition, by irradiation, or by heating. Sterilization may be effected, for example, by filtration through a 0.2 μm pore size filter. Other methods of sterilizing well known to those skilled in the art can also be employed.

To formulate aqueous parenteral dosage forms, an aqueous medium, e.g., physiological saline or purified water, paclitaxel solubilizers, and any additional components are mixed in sanitized equipment, filtered, and packaged according to well known methods in the art (for a discussion see e.g., *Remington: the Science and Practice of Pharmacy*, Alfonso R. Gennaro ed., Mack Publishing Co. Easton, Pa., 19th ed., 1995, Chapter 87). For parenteral administration the dosage will, of course, vary with the potency of the particular active based on potency, the patient weight, and the nature of the patient's condition. The preferred dosage for intravenous administration is that listed in The Physician's Desk Reference, 54th edition, 881–887, Medical Economics Company (2000). Dosages typically fall in the range of about 135 mg/m$^2$ to 400 mg/m$^2$, preferably 175 mg/m$^2$, more preferably, 200 mg/m$^2$. An oncologist skilled in the art of cancer treatment will be able to ascertain appropriate protocols for effective administration of the formulations of the invention by referring to the earlier studies of paclitaxel, derivatives, and pharmaceutically acceptable salts thereof or the dosages listed in medical reference books.

Formulations of the invention for oral delivery are preferably in the form of capsules, tablets, pills, soft-gel capsules, emulsions, solutions, or suspensions. Oral compositions can include standard vehicles, excipients, and diluents. Orally administered formulations of the invention can optionally include one or more sweetening agents and one or more flavoring agents to provide a pharmaceutically palatable preparation. A therapeutically effective oral dosage for formulations of the invention is determined by standard clinical techniques according to the judgment of a medical practitioner. For example, in addition to information provided in medical reference books and pharmaceutical literature, well-known in vitro or in vivo assays can be used to help identify optimal dosages.

To formulate and administer transdermal dosage forms, well known transdermal delivery devices such as patches can be used (Ghosh, T. K.; Pfister, W. R.; Yum, S. I. *Transdermal and Topical Drug Delivery Systems*, Interpharm Press, Inc. p. 249–297, incorporated herein by reference). For example, a reservoir type patch design can comprise a backing film coated with an adhesive, and a reservoir compartment comprising a formulation of the invention, that is separated from the skin by a semipermeable membrane (e.g., U.S. Pat. No. 4,615,699, incorporated herein by reference). The adhesive coated backing layer extends around the reservoir's boundaries to provide a concentric seal with the skin and hold the reservoir adjacent to the skin.

To formulate and administer local dosage forms, well known mediums such as lotions, creams, and ointments can be used.

The present formulations can include additional actives and thus can serve as base formulation for combination therapy. Such additional actives can be included and distributed in the formulation itself (e.g., pre-diluted or in a form for reconstitution) or added to the formulation prior to administration. For example, the formulations of the invention and other actives can be combined in an i.v. bag prior to administration. Additional actives can be any pharmaceutical conventionally administered with paclitaxel, for example, other chemotherapeutics, such as, but not limited to, cisplatin, carboplatin, tamoxifen, epirubicin, leuprolide, bicalutamide, goserelin implant, irinotecan, gemcitabine, and sargramostim or pharmaceutically acceptable salts thereof, preferably cisplatin. Thus, the formulations of the invention encompass formulations comprising active, the paclitaxel solubilizers of the invention, and other actives suitable for co-administration with paclitaxel.

The formulations of the invention can be packaged and distributed as a non-aqueous liquid-solution concentrates for dilution in an aqueous medium prior to administration. For example, the present formulations in liquid-concentrate form or in the form of a lyophilized solid can be added to an i.v. bag and diluted with an aqueous medium prior to intravenous infusion. Preferably, such concentrates comprise a non-aqueous solvent, the active, and one or more of the paclitaxel solubilizers of the invention. Preferably, the non-aqueous solvent is an organic solvent, such as ethanol. Thus, the formulations of the invention in liquid-concentrate form can be packaged as ethanol solutions, for example, packaged in a multi-unit-dose vial containing 30 mg paclitaxel, the paclitaxel solubilizers, and about 0.2 ml to about 3 ml ethanol or a multi-unit-dose vial containing 100 mg paclitaxel, the paclitaxel solubilizers, and about 0.6 ml to 10 ml of ethanol.

The formulations of the invention, can be distributed in containers that allow rapid dissolution of the formulation upon reconstitution with appropriate sterile diluents, in situ, giving an appropriate sterile solution of desired active concentration for administration. As used herein, the term "suitable containers" means a container capable of maintaining a sterile environment, such as a vial, package, or bottle, capable of delivering a vacuum dried product hermetically sealed by a stopper means. Additionally, suitable containers implies appropriateness of size, considering the volume of solution to be held upon reconstitution of the vacuum dried composition; and appropriateness of container material, generally Type I glass. The stopper means employed, e.g., sterile rubber closures or an equivalent, should be understood to be that which provides the aforementioned seal, but which also allows entry for the purpose of introduction of diluent, e.g., sterile Water for Injection, USP, Normal Saline, USP, or 5% Dextrose in Water, USP, for the reconstitution of the desired active solution. These and other aspects of the suitability of containers for pharmaceutical products such as those of the invention are well known to those skilled in the practice of pharmaceutical arts.

The present invention will be further understood by reference to the following non-limiting examples. The following examples are provided for illustrative purposes only and are not to be construed as limiting the invention scope of the invention in any manner.

5. EXAMPLES

Example 1

Preparation and Identification of Aqueous Paclitaxel Formulations with Enhanced Solubility A plurality of aqueous formulations, each containing paclitaxel and various combinations and concentrations of the excipients listed in Table 1 below were prepared and systematically analyzed for their ability to dissolve paclitaxel.

The GRAS ("generally regarded as safe") excipients listed in Table 1 are all obtainable from Sigma-Aldrich Fine Chemicals, BASF, or other commercial suppliers.

TABLE 1

| | Excipients Used in the Examples |
|---|---|
| 1 | γ-Cyclodextrin |
| 2 | β-Cyclodextrin |
| 3 | Diethanolamine |
| 4 | Propyleneglycol |
| 5 | Glycerin |
| 6 | Poloxomer ® 188 |
| 7 | Poloxomer ® 237 |
| 8 | Poloxomer ® 338 |
| 9 | Poloxomer ® 407 |
| 10 | Polyethyleneglycol 300 (PEG-300) |
| 11 | Polyethyleneglycol 600 (PEG-600) |
| 12 | Polyethyleneglycol 1000 (PEG-1000) |
| 13 | Polyethyleneglycol 4000 (PEG-4000) |
| 14 | Polysorbate 20 |
| 15 | Polysorbate 80 |
| 16 | Polyethyleneglycol-20 monostearate (PEG-20 monostearate) |
| 17 | Polyethyleneglycol-40 monostearate (PEG-40 monostearate) |

TABLE 1-continued

| | Excipients Used in the Examples |
|---|---|
| 18 | Polyethyleneglycol-50 monostearate (PEG-50 monostearate) |
| 19 | Choline chloride Polyethyleneglycol-20 glyceryl monooleate (PEG-20 glyceryl monooleate) |
| 20 | Sodium caprylate |
| 21 | Polyethyleneglycol-100 monostearate (PEG-100 monostearate) |
| 22 | Povidone |
| 23 | Deoxycholoate |
| 24 | Laureth-23 |
| 25 | Isosorbide dimethyl ether |
| 26 | Polyethyleneglycol-20 monooleate (PEG-20 monooleate) |
| 27 | Polyethyleneglycol-20 monolaurate (PEG-20 monolaurate) |
| 28 | Polyethyleneglycol-tetrahydrofurfuryl ether (PEG-tetrahydrofurfuryl) |
| 29 | octoxynol-9 |
| 30 | 2-pyrrolidone |
| 31 | Benzethonium chloride |
| 32 | Benzalkonium chloride |
| 33 | cetrimide |
| 34 | Polyethyleneglycol-1,2-diacyl-sn-glycerol-3-phosphoethanolamine-N-[methoxy(polyethylene glycol)-2000] (PEG-DSPE) |
| 35 | Polyvinyl alcohol |
| 36 | tocophersolan |
| 37 | Sodium lauryl sulfate (SDS) |
| 38 | Protamine sulfate |
| 39 | Laureth-23 |
| 40 | Polyethyleneglycol-20 glyceryl monolaurate (PEG-20 glyceryl monolaurate) |

Preparation of Formulations with Improved Solubilities

A stock solution comprising about 10 milligrams paclitaxel per milliliter ethanol was prepared. Then a plurality of excipients were selected from Table 1 and each selected excipient was prepared as an aqueous solution, at various concentrations, for example, as three physiological-saline stock solutions each at one of three set concentrations, e.g. about 120 milligrams/milliliter, about 60 milligrams/milliliter, and about 30 milligrams/milliliter. Then all permutations of formulations that each comprise about 12 µl of the paclitaxel/ethanol solution (about 120 µg of paclitaxel per sample well) and about 90 µl of one to three of the excipient stock solutions were prepared.

All permutations of excipients stock solutions and paclitaxel were generated using the MATLAB program formulating software (commercially available from Mathworks, Natick, Mass.). The permutations so generated were downloaded into a Microsoft EXCEL spread sheet and from this spread sheet, a worklist was constructed according to standard programming methods well known to those skilled in the art. The work-list is then used to direct the Genesis liquid-handling device to prepare the various permutations of excipients and paclitaxel generated by MATLAB. The worklist combines the formulation output of the MATLAB program with Genesis-appropriate commands (as found in the Genesis operating manual) in a file format that is directly readable by the Genesis device. For example, the number of possible unique combinations with 120 excipient stock solutions is:

$$\frac{(120+3-1)!}{3!(120-1)!} = 295,240$$

giving a grand total of 295,240 unique formulations. The formulations were prepared in DYNEX 96 sample well polystyrene plates (available from Thermo Labsystems Oy, Helsinki, Finland). Each sample well has a volume of 250 μl. Each sample formulation generated by the MATLAB program was prepared in triplicate by adding about 12 μl of the paclitaxel/ethanol solution and about 30 μl of three of the excipient stock solution to each sample well. The stock solutions were added using a Genesis liquid-handling device (Tecan-US, RTP, NC). The force provided by adding the excipient via the Genesis liquid-handling device was sufficient to adequately mix the components. The plates were sealed with aluminum sealing tapes and incubated at 25° C. for 48 hours before they were measured on a UV plate reader at 500 nm (SpectraMax Plus, Molecular Devices, Sunnyvale, Calif.).

Results

The screening results, measured as turbidity at 500 nm for all of the samples were imported into a data analysis and visualization program Spotfire (Spotfire, Cambridge, Mass.) and samples that reproducibly (% standard deviation <5%) demonstrated an absorbance below 0.045 were selected as hits. An absorbance below 0.045 indicates that the paclitaxel was completely dissolved, i.e., the paclitaxel concentration was 1.2 mg/ml, and stayed dissolved for 48 hours. The selected formulations along with concentrations of the paclitaxel solubilizers are listed in Table 2 below. Each of these examples can readily be used to formulate paclitaxel into a suitable injectable dosage form.

The chemical stability of the paclitaxel formulations in Table 2 was analyzed using a Waters Alliance 2790 HPLC equipped with a Waters 996 Photo Diode Array Detector. The separation was carried out on a Phenomenex Curosil Pentafluorphenyl column (150×3.2 mm, 3 m) with a mobile phase of 55% water and 45% acetonitrile, held isocratic at a flow rate of 0.5 ml/min. A control solution of paclitaxel (0.1 mg/ml) for comparison was prepared from a stock solution of 1 mg/ml in ethanol by sub-dilution into acetonitrile. Each of the formulations of paclitaxel were diluted in acetonitrile to a concentration of approximately 0.1 mg/ml before HPLC analysis and absorbance was measured at 229 nm. The chromatograph for each formulation was compared with the control solution. No degradation of Paclitaxel was observed for the selected formulations, even after 48 hours incubation at RT in physiological saline, establishing chemical stability of the formulations of the invention. Using this general procedure with the 40 excipients listed in Table 1, the formulations listed in Table 2 were selected as stable and capable of dissolving paclitaxel in an aqueous medium to a concentration of 1.2 mg/ml.

TABLE 2

Selected Formulations

| Abs | Excipient | Conc. mg/ml | Excipient | Conc. mg/ml | Excipient | Conc. mg/ml |
|---|---|---|---|---|---|---|
| 0.039 | polysorbate 80 | 18 | otoxynol-9 | 18 | benzalkonium chloride | 18 |
| 0.039 | polysorbate 80 | 18 | otoxynol-9 | 18 | cetrimide | 18 |
| 0.039 | polysorbate 80 | 36 | otoxynol-9 | 36 | PEG-20 monolaurate | 36 |
| 0.039 | polysorbate 80 | 36 | otoxynol-9 | 36 | PEG-20 monooleate | 36 |
| 0.040 | polysorbate 80 | 36 | otoxynol-9 | 72 | | |
| 0.039 | polysorbate 20 | 36 | otoxynol-9 | 36 | PEG-20 monolaurate | 36 |
| 0.039 | polysorbate 20 | 36 | otoxynol-9 | 72 | | |
| 0.039 | polysorbate 20 | 18 | Sodium caprylate | 18 | cetrimide | 18 |
| 0.040 | polysorbate 80 | 72 | PEG-20 monooleate | 36 | | |
| 0.040 | polysorbate 80 | 36 | PEG-20 monooleate | 72 | | |
| 0.040 | polysorbate 20 | 36 | PEG-20 monooleate | 72 | | |
| 0.040 | polysorbate 80 | 72 | PEG-20 monolaurate | 36 | | |
| 0.040 | polysorbate 80 | 36 | PEG-20 monolaurate | 72 | | |
| 0.040 | polysorbate 20 | 36 | PEG-20 monolaurate | 72 | | |
| 0.039 | polysorbate 80 | 18 | benzethonium chloride | 18 | PEG 1000 | 18 |
| 0.039 | polysorbate 20 | 36 | 2-pyrrolidone | 36 | octoxynol-9 | 36 |
| 0.039 | octoxynol-9 | 36 | benzalkonium chloride | 18 | | |
| 0.039 | octoxynol-9 | 36 | PEG-20 monolaurate | 36 | PEG-20 monooleate | 36 |
| 0.038 | octoxynol-9 | 72 | PEG-20 monolaurate | 36 | | |
| 0.040 | octoxynol-9 | 36 | PEG-20 monolaurate | 72 | | |
| 0.040 | octoxynol-9 | 72 | PEG-20 monooleate | 36 | | |
| 0.038 | octoxynol-9 | 108 | | | | |
| 0.040 | Isosorbide dimethyl ether | 36 | octoxynol-9 | 36 | PEG-20 monolaurate | 36 |
| 0.039 | Isosorbide dimethyl ether | 36 | octoxynol-9 | 72 | | |
| 0.039 | benzethonium chloride | 36 | octoxynol-9 | 18 | | |
| 0.039 | PEG-tetrahydrofurfuryl ether | 36 | octoxynol-9 | 36 | PEG-20 monolaurate | 36 |
| 0.039 | benzethonium chloride | 18 | octoxynol-9 | 36 | | |
| 0.039 | Sodium caprylate | 18 | octoxynol-9 | 18 | benzalkonium chloride | 18 |
| 0.038 | benzethonium chloride | 18 | octoxynol-9 | 18 | cetrimide | 18 |
| 0.038 | SDS | 36 | octoxynol-9 | 18 | | |
| 0.039 | Povidone | 18 | SDS | 18 | β-cyclodextrin | 4.5 |
| 0.038 | Sodium caprylate | 18 | SDS | 36 | | |

TABLE 2-continued

Selected Formulations

| Abs | Excipient | Conc. mg/ml | Excipient | Conc. mg/ml | Excipient | Conc. mg/ml |
|---|---|---|---|---|---|---|
| 0.039 | benzethonium chloride | 36 | propylene glycol | 18 | | |
| 0.038 | SDS | 36 | propylene glycol | 18 | | |
| 0.039 | benzethonium chloride | 36 | cetrimide | 18 | | |
| 0.040 | benzethonium chloride | 36 | benzalkonium chloride | 18 | | |
| 0.038 | cetrimide | 36 | benzalkonium chloride | 18 | | |
| | PEG-20 monooleate | 108 | | | | |
| 0.040 | | | | | | |
| 0.039 | benzethonium chloride | 54 | | | | |
| 0.038 | SDS | 54 | | | | |
| 0.040 | tocophersolan | 60 | protamine sulfate | 3.06 | | |
| 0.040 | tocophersolan | 48 | protamine sulfate | 1.836 | | |
| 0.040 | tocophersolan | 60 | PEG-20 monostearate | 30 | | |
| 0.040 | tocophersolan | 60 | PEG-20 monostearate | 18 | | |
| 0.042 | tocophersolan | 30 | PEG-20 monostearate | 60 | | |
| 0.039 | tocophersolan | 48 | PEG-20 monostearate | 30 | | |
| 0.040 | tocophersolan | 30 | PEG-20 monostearate | 48 | | |
| 0.040 | tocophersolan | 48 | PEG-20 monostearate | 18 | | |
| 0.039 | tocophersolan | 36 | PEG-20 monostearate | 30 | | |
| 0.040 | tocophersolan | 60 | PEG 300 | 102 | | |
| 0.040 | tocophersolan | 60 | PEG 300 | 61.2 | | |
| 0.040 | tocophersolan | 48 | PEG 300 | 61.2 | | |
| 0.040 | tocophersolan | 90 | | | | |
| 0,040 | tocophersolan | 78 | | | | |
| 0.040 | tocophersolan | 66 | | | | |
| 0.040 | tocophersolan | 54 | | | | |
| 0.040 | polysorbate 80 | 30 | tocophersolan | 60 | | |
| 0.041 | polysorbate 80 | 48 | tocophersolan | 30 | | |
| 0.040 | polysorbate 80 | 18 | tocophersolan | 60 | | |
| 0.041 | polysorbate 80 | 36 | tocophersolan | 30 | | |
| 0.040 | polysorbate 80 | 36 | tocophersolan | 18 | | |
| 0.041 | polysorbate 80 | 30 | tocophersolan | 30 | PEG-20 monostearate | 18 |
| 0.040 | polysorbate 80 | 30 | tocophersolan | 18 | PEG-20 monostearate | 30 |
| 0.041 | polysorbate 80 | 18 | tocophersolan | 30 | PEG-20 monostearate | 30 |
| 0.043 | polysorbate 80 | 18 | tocophersolan | 30 | protamine sulfate | 3.06 |
| 0.040 | polysorbate 20 | 30 | tocophersolan | 60 | | |
| 0.040 | polysorbate 20 | 18 | tocophersolan | 60 | | |
| 0.039 | polysorbate 20 | 36 | tocophersolan | 30 | | |
| 0.039 | PEG-20 monooleate | 30 | tocophersolan | 60 | | |
| 0.039 | PEG-20 monooleate | 30 | tocophersolan | 48 | | |
| 0.040 | PEG-20 monooleate | 18 | tocophersolan | 60 | | |
| 0.039 | PEG-20 monooleate | 30 | tocophersolan | 30 | PEG-20 monostearate | 30 |
| 0.039 | PEG-20 monolaurate | 30 | tocophersolan | 60 | | |
| 0.040 | choline chloride | 48 | tocophersolan | 30 | | |
| 0.040 | choline chloride | 30 | tocophersolan | 48 | | |
| 0.040 | choline chloride | 18 | tocophersolan | 60 | | |
| 0.040 | choline chloride | 18 | tocophersolan | 48 | | |
| 0.039 | laureth-23 | 30 | tocophersolan | 60 | | |
| 0.039 | laureth-23 | 30 | tocophersolan | 48 | | |
| 0.041 | laureth-23 | 18 | tocophersolan | 48 | | |
| 0.040 | laureth-23 | 18 | tocophersolan | 30 | PEG-20 monostearate | 18 |
| 0.039 | polysorbate 80 | 18 | PEG-20 monooleate | 18 | tocophersolan | 30 |
| 0.040 | polysorbate 80 | 18 | choline chloride | 30 | tocophersolan | 30 |
| 0.040 | polysorbate 80 | 30 | PEG-20 monooleate | 60 | | |
| 0.042 | PEG-20 monostearate | 66 | | | | |
| 0.040 | PEG-20 monooleate | 30 | PEG-20 monostearate | 60 | | |
| 0.040 | PEG-20 monooleate | 90 | | | | |
| 0.039 | laureth-23 | 18 | PEG-20 monooleate | 18 | tocophersolan | 30 |
| 0.038 | PEG-20 glyceryl monooleate | 100 | polysorbate 80 | 40 | | |
| 0.039 | PEG-20 glyceryl monooleate | 100 | polysorbate 80 | 60 | | |
| 0.039 | PEG-20 glyceryl monooleate | 100 | polysorbate 80 | 80 | | |
| 0.040 | PEG-20 glyceryl monooleate | 100 | PEG-20 monooleate | 60 | | |
| 0.039 | PEG-20 glyceryl monooleate | 100 | PEG-20 monooleate | 80 | | |
| 0.039 | PEG-20 glyceryl monooleate | 100 | PEG-20 monolaurate | 60 | | |

TABLE 2-continued

Selected Formulations

| Abs | Excipient | Conc. mg/ml | Excipient | Conc. mg/ml | Excipient | Conc. mg/ml |
|---|---|---|---|---|---|---|
| 0.040 | PEG-20 glyceryl monooleate | 100 | PEG-20 monolaurate | 80 | | |
| 0.039 | PEG-20 glyceryl monooleate | 100 | PEG-20 monolaurate | 40 | | |
| 0.040 | PEG-20 glyceryl monooleate | 100 | PEG-20 monolaurate | 20 | | |
| 0.038 | PEG-20 glyceryl monooleate | 100 | polysorbate 20 | 40 | | |
| 0.039 | PEG-20 glyceryl monooleate | 100 | polysorbate 20 | 60 | | |
| 0.039 | PEG-20 glyceryl monooleate | 100 | polysorbate 20 | 80 | | |
| 0.038 | PEG-20 glyceryl monooleate | 100 | tocophersolan | 20 | | |
| 0.038 | PEG-20 glyceryl monooleate | 100 | tocophersolan | 40 | | |
| 0.038 | PEG-20 glyceryl monooleate | 100 | tocophersolan | 60 | | |
| 0.039 | PEG-20 glyceryl monooleate | 100 | tocophersolan | 80 | | |
| 0.039 | PEG-20 glyceryl monooleate | 80 | tocophersolan | 100 | | |
| 0.039 | PEG-20 glyceryl monooleate | 60 | tocophersolan | 100 | | |
| 0.040 | PEG-20 glyceryl monooleate | 40 | tocophersolan | 100 | | |
| 0.039 | PEG-20 glyceryl monooleate | 20 | tocophersolan | 100 | | |
| 0.040 | tocophersolan | 100 | | | | |
| 0.038 | PEG-20 glyceryl monolaurate | 100 | tocophersolan | 60 | | |
| 0.039 | PEG-20 glyceryl monolaurate | 100 | tocophersolan | 80 | | |
| 0.039 | PEG-20 glyceryl monolaurate | 80 | tocophersolan | 100 | | |
| 0.039 | PEG-20 glyceryl monolaurate | 60 | tocophersolan | 100 | | |
| 0.040 | PEG-20 glyceryl monolaurate | 40 | tocophersolan | 100 | | |
| 0.039 | PEG-20 glyceryl monolaurate | 20 | tocophersolan | 100 | | |

Excipients classes that were present in at least 10 formulations listed in Table 2 above and gave stable paclitaxel solutions were selected as paclitaxel solubilizers of the invention (i.e., PEG-vitamin Es, quaternary ammonium salts, PEG-monoacid fatty esters, PEG-glyceryl fatty esters, polysorbates, and PEG-fatty alcohols) first, because they were present in formulations that dissolved paclitaxel to a concentration of about 1.2 mg/ml and, second, by appearing at high frequency, indicated that they interacted with paclitaxel or the other components to facilitate dissolution of paclitaxel in an aqueous medium.

TABLE 3

Paclitaxel Solubilizers of the Invention

| Excipient Class | Hits |
|---|---|
| PEG-Vitamin Es | 59 |
| Quaternary ammonium salts | 14 |
| PEG-monoacid fatty esters | 44 |
| PEG-glyceryl fatty esters | 20 |
| Polysorbates | 38 |
| PEG-fatty alcohols | 27 |

Preferred paclitaxel solubilizers are PEG-Vitamin Es, such as tocophersolan; polysorbates, such as polysorbates 80 and 20; PEG-monoacid fatty esters, such as PEG-20 monooleate, PEG-20 monolaurate, and PEG-20 monostearate; PEG-glyceryl fatty esters, such as PEG-20 glyceryl monooleate, PEG-20 glyceryl monostearate, and PEG-20 glyceryl monolaurate; and PEG-fatty alcohols, such as octoxynols (e.g., octoxynol-9), oleths, and laureths (e.g., laureth-23).

The data in Table 2 was further analyzed with respect to the paclitaxel solubilizers of the invention (Table 3) to determine combinations of excipients useful for solubilizing and administering paclitaxel, derivatives, and salts thereof.

Table 4 below lists excipients along with the excipient class, that appeared as a component with a PEG-vitamin E in the selected formulations of Table 2 at a high frequency (i.e., at least 4 times).

TABLE 4

Excipient Classes That in Combination with a PEG-vitamin E provide Formulations with a High Propensity to Dissolve Paclitaxel

| Class | Excipient | Excipient hits | Class hits |
|---|---|---|---|
| PEG-monoacid fatty | PEG-20 monooleate | 6 | 19 |
| | PEG-20 | 12 | |

TABLE 4-continued

Excipient Classes That in Combination with a PEG-vitamin E provide Formulations with a High Propensity to Dissolve Paclitaxel

| Class | Excipient | Excipient hits | Class hits |
|---|---|---|---|
| esters | monostearate PEG-20 monolaurate | 1 | |
| PEG-glyceryl fatty esters | PEG-20 glyceryl monooleate | 8 | 14 |
| | PEG-20 glyceryl monolaurate | 6 | |
| Polysorbates | polysorbate 20 | 3 | 14 |
| | polysorbate 80 | 11 | |
| PEG-fatty alcohols | octoxynol-9 | 0 | 5 |
| | laureth-23 | 5 | |

The data in Table 4 above demonstrates that PEG-vitamin Es in combination with excipient classes PEG-monoacid fatty esters, PEG-glyceryl fatty esters, polysorbates, or PEG-fatty alcohols interact to provide formulations useful for solubilizing paclitaxel.

Table 5 below lists excipients, along with the excipient class, that appeared as a component with a quaternary ammonium salt in the selected formulations of Table 2 at a high frequency.

TABLE 5

Excipient Classes That in Combination with a Quaternary Ammonium Salt Provide Formulations with a High Propensity to Dissolve Paclitaxel

| Class | Excipient | Excipient hits | Class hits |
|---|---|---|---|
| Polysorbates | polysorbate 20 | 1 | 4 |
| | polysorbate 80 | 3 | |
| PEG-fatty alcohols | octoxynol-9 | 8 | 8 |
| | laureth-23 | 0 | |

The data in Table 5 above demonstrates that quaternary ammonium salts in combination with excipient classes polysorbates or PEG-fatty alcohols interact to provide formulations useful for solubilizing paclitaxel.

Table 6 below lists excipients, along with the excipient class, that appeared as a component with a PEG-monoacid fatty esters in the selected formulations of Table 2 at a high frequency.

TABLE 6

Excipient Classes That in Combination with a PEG-monoacid Fatty Ester Provide Formulations with a High Propensity to Dissolve Paclitaxel

| Class | Excipient | Excipient hits | Class hits |
|---|---|---|---|
| PEG-Vitamin Es | tocophersolan | 18 | 18 |
| Polysorbates | polysorbate 20 | 2 | 11 |
| | polysorbate 80 | 9 | |
| PEG-fatty alcohols | octoxynol-9 | 4 | 6 |
| | laureth-23 | 2 | |
| PEG-glyceryl fatty esters | PEG-20 glyceryl monooleate | 6 | 6 |
| | PEG-20 glyceryl monolaurate | 0 | |

The data in Table 6 above demonstrates that PEG-monoacid fatty esters in combination with excipient classes PEG-vitamin Es, polysorbates, PEG-fatty alcohols, or PEG-glyceryl fatty esters interact to provide formulations useful for solubilizing paclitaxel.

Table 7 below lists excipients, along with the excipient class, that appeared as a component with a polysorbate in the selected formulations of Table 2 at a high frequency.

TABLE 7

Excipient Classes That in Combination with a PEG-Glyceryl fatty esters Provide Formulations with a High Propensity to Dissolve Paclitaxel

| Class | Excipient | Excipient hits | Class hits |
|---|---|---|---|
| PEG-Vitamin Es | tocophersolan | 14 | 14 |
| Polysorbates | polysorbate 20 | 3 | 6 |
| | polysorbate 80 | 3 | |
| PEG-monoacid fatty esters | PEG-20 monooleate | 2 | 6 |
| | PEG-20 monostearate | 0 | |
| | PEG-20 monolaurate | 4 | |

The data in Table 7 above demonstrates that PEG-glyceryl fatty esters in combination with excipient classes PEG-vitamin Es, polysorbates, or PEG-monoacid fatty esters interact to provide formulations useful for solubilizing paclitaxel.

Table 8 below lists excipients, along with the excipient class, that appeared as a component with a polysorbate in the selected formulations of Table 2 at a high frequency.

TABLE 8

Excipient Classes That in Combination with a Polysorbate Provide Formulations with a High Propensity to Dissolve Paclitaxel

| Class | Excipient | Excipient hits | Class hits |
|---|---|---|---|
| PEG-Vitamin Es | tocophersolan | 14 | 14 |
| Quaternary ammonium salts | benzalkonium chloride | 1 | 4 |
| | benzethonium chloride | 1 | |
| | cetrimide | 2 | |
| PEG-monoacid fatty esters | PEG-20 monooleate | 5 | 13 |
| | PEG-20 monostearate | 3 | |
| | PEG-20 monolaurate | 5 | |
| PEG-glyceryl fatty esters | PEG-20 glyceryl monooleate | 6 | 6 |
| | PEG-20 glyceryl monolaurate | 0 | |
| PEG-fatty alcohols | octoxynol-9 | 8 | 8 |
| | laureth-23 | 0 | |

The data in Table 8 above demonstrates that polysorbates in combination with excipient classes PEG-vitamin Es, quaternary ammonium salts, PEG-monoacid fatty esters, PEG-glyceryl fatty esters, or PEG-fatty alcohols, interact to provide formulations useful for solubilizing paclitaxel.

Table 9 below lists excipients, along with the excipient class, that appeared as a component with a PEG-fatty alcohol in the formulations of Table 2 at a high frequency.

TABLE 9

Excipient Classes That in Combination with a PEG-fatty Alcohol Provide Formulations with a High Propensity to Dissolve Paclitaxel

| Class | Excipient | Excipient hits | Class hits |
|---|---|---|---|
| PEG-Vitamin Es | tocophersolan | 5 | 5 |
| Quaternary ammonium salts | benzalkonium chloride | 3 | 8 |
| | benzethonium chloride | 3 | |
| | cetrimide | 2 | |

TABLE 9-continued

Excipient Classes That in Combination with
a PEG-fatty Alcohol Provide Formulations with
a High Propensity to Dissolve Paclitaxel

| Class | Excipient | Excipient hits | Class hits |
|---|---|---|---|
| PEG-monoacid fatty esters | PEG-20 monooleate | 4 | 12 |
|  | PEG-20 monostearate | 1 |  |
|  | PEG-20 monolaurate | 7 |  |
| Polysorbates | polysorbate 20 | 3 | 8 |
|  | polysorbate 80 | 5 |  |

The data in Table 9 above demonstrates that PEG-fatty alcohols in combination with excipient classes PEG-vitamin Es, quaternary ammonium salts, PEG-monoacid fatty esters, or polysorbates interact to provide formulations useful for solubilizing paclitaxel.

Example 2

Preparation of Liquid-Concentrate Paclitaxel Formulations with Enhanced Aqueous Solubility The following liquid-concentrate paclitaxel formulations were prepared by mixing paclitaxel, the paclitaxel solubilizers, and additional components using standard pharmaceutical-formulation procedures.

Formulation A

| Component | Weight | % weight |
|---|---|---|
| Paclitaxel | 6 mg | 0.6% |
| PEG-400 | 294 mg | 29.2% |
| Polysorbate 80 | 485 mg | 48.1% |
| Ethanol | 221 mg | 21.9% |
| Citric acid | 2 mg | 0.2% |

Formulation B

| Component | Weight | % weight |
|---|---|---|
| Paclitaxel | 6 mg | 0.6% |
| PEG-20 glyceryl monooleate | 500 mg | 49.6% |
| Ethanol | 300 mg | 29.8% |
| Polysorbate 80 | 200 mg | 19.8% |
| Citric acid | 2 mg | 0.2% |

Formulation C

| Component | Weight | % weight |
|---|---|---|
| Paclitaxel | 6 mg | 0.6% |
| PEG-20 glyceryl monooleate | 500 mg | 49.6% |
| Ethanol | 400 mg | 39.7% |
| Vitamin E TPGS | 100 mg | 9.9% |
| Citric acid | 2 mg | 0.2% |

Formulation D

| Component | Weight | % weight |
|---|---|---|
| Paclitaxel | 6 mg | 0.6% |
| PEG-20 glyceryl monooleate | 500 mg | 49.6 |
| Ethanol | 300 mg | 29.8 |
| PEG-20 monolaurate | 200 mg | 19.8 |
| Citric acid | 2 mg | 0.2% |

Formulation E

| Component | Weight | % weight |
|---|---|---|
| Paclitaxel | 6 mg | 0.6% |
| PEG-20 glyceryl monooleate | 500 mg | 49.6% |
| Ethanol | 300 mg | 29.8% |
| Polysorbate 20 | 200 mg | 19.8% |
| Citric acid | 2 mg | 0.2% |

Formulation F

| Component | Weight | % weight |
|---|---|---|
| Paclitaxel | 6 mg | 0.6% |
| PEG-20 glyceryl monooleate | 500 mg | 49.6% |
| Ethanol | 200 mg | 19.8% |
| PEG-20 monooleate | 300 mg | 29.8% |
| Citric acid | 2 mg | 0.2% |

Formulation G

| Component | Weight | % weight |
|---|---|---|
| Paclitaxel | 6 mg | 0.6% |
| Ethanol | 500 mg | 49.6% |
| Vitamin E TPGS | 500 mg | 49.6% |
| Citric acid | 2 mg | 0.2% |

Formulation H

| Component | Weight | % weight |
|---|---|---|
| Paclitaxel | 6 mg | 0.6% |
| Ethanol | 400 mg | 39.7% |
| Vitamin E TPGS | 500 mg | 49.6% |
| PEG-400 | 100 mg | 9.9% |
| Citric acid | 2 mg | 0.2% |

Formulation I

| Component | Weight | % weight |
|---|---|---|
| Paclitaxel | 6 mg | 0.6% |
| Ethanol | 400 mg | 39.7% |
| Vitamin E TPGS | 500 mg | 49.6% |
| PEG-20 monooleate | 100 mg | 9.9% |
| Citric acid | 2 mg | 0.2% |

Formulation J

| Component | Weight | % weight |
|---|---|---|
| Paclitaxel | 6 mg | 0.6% |
| Ethanol | 400 mg | 39.7% |
| Vitamin E TPGS | 500 mg | 49.6% |
| Polysorbate 80 | 100 mg | 9.9% |
| Citric acid | 2 mg | 0.2% |

Formulation K

| Component | Weight | % weight |
|---|---|---|
| Paclitaxel | 6 mg | 0.6% |
| Ethanol | 400 mg | 39.7% |
| Vitamin E TPGS | 500 mg | 49.6% |
| Polysorbate 20 | 100 mg | 9.9% |
| Citric acid | 2 mg | 0.2% |

Formulation L

| Component | Weight | % weight |
|---|---|---|
| Paclitaxel | 6 mg | 0.6% |
| Ethanol | 400 mg | 39.7% |
| Vitamin E TPGS | 500 mg | 49.6% |
| PEG-20 monolaurate | 100 mg | 9.9% |
| Citric acid | 2 mg | 0.2% |

Formulation M

| Component | Weight | % weight |
|---|---|---|
| Paclitaxel | 6 mg | 0.6% |
| Ethanol | 559 mg | 55.4% |
| Polysorbate 80 | 294 mg | 29.2% |
| PEG-20 monooleate | 147 mg | 14.6% |
| Citric acid | 2 mg | 0.2% |

Formulation N

| Component | Weight | % weight |
|---|---|---|
| Paclitaxel | 6 mg | 0.6% |
| PEG-400 | 500 mg | 49.6% |
| Polysorbate 80 | 300 mg | 29.8% |
| Ethanol | 200 mg | 19.9% |
| Citric acid | 2 mg | 0.2% |

Formulation O

| Component | Weight | % weight |
|---|---|---|
| Paclitaxel | 6 mg | 0.6% |
| PEG-400 | 500 mg | 49.6% |
| Ethanol | 150 mg | 14.9% |

-continued

Formulation O

| Component | Weight | % weight |
|---|---|---|
| Polysorbate 80 | 350 mg | 34.7% |
| Citric acid | 2 mg | 0.2% |

Formulation P

| Component | Weight | % weight |
|---|---|---|
| Paclitaxel | 6 mg | 0.6% |
| PEG-20 glyceryl monooleate | 400 mg | 39.7% |
| Ethanol | 400 mg | 39.7% |
| Polysorbate 80 | 200 mg | 19.9% |
| Citric acid | 2 mg | 0.2% |

Formulation Q

| Component | Weight | % weight |
|---|---|---|
| Paclitaxel | 6 mg | 0.6% |
| PEG-20 glyceryl monooleate | 300 mg | 29.8% |
| Ethanol | 500 mg | 49.6% |
| Polysorbate 80 | 200 mg | 19.9% |
| Citric acid | 2 mg | 0.2% |

Formulation R

| Component | Weight | % weight |
|---|---|---|
| Paclitaxel | 6 mg | 0.6% |
| PEG-20 glyceryl monooleate | 500 mg | 49.6% |
| Ethanol | 400 mg | 39.7% |
| Polysorbate 80 | 100 mg | 9.9% |
| Citric acid | 2 mg | 0.2% |

Formulation S

| Component | Weight | % weight |
|---|---|---|
| Paclitaxel | 6 mg | 0.6% |
| PEG-20 glyceryl monooleate | 600 mg | 59.5% |
| Ethanol | 400 mg | 39.7% |
| Citric acid | 2 mg | 0.2% |

Formulation T

| Component | Weight | % weight |
|---|---|---|
| Paclitaxel | 6 mg | 0.6% |
| PEG-20 glyceryl monooleate | 550 mg | 54.5% |
| Ethanol | 450 mg | 44.6% |
| Citric acid | 2 mg | 0.2% |

Formulation U

| Component | Weight | % weight |
|---|---|---|
| Paclitaxel | 6 mg | 0.6% |
| PEG-20 glyceryl monooleate | 500 mg | 49.6% |
| Ethanol | 500 mg | 49.6% |
| Citric acid | 2 mg | 0.2% |

Formulation V

| Component | Weight | % weight |
|---|---|---|
| Paclitaxel | 6 mg | 0.6% |
| Polyethylene Glycol 400 | 294 mg | 29.2% |
| Polysorbate 80 | 529 mg | 52.5% |
| Ethanol | 176 mg | 17.5% |
| Citric Acid | 2 mg | 0.2% |

Formulation W

| Component | Weight | % weight |
|---|---|---|
| Paclitaxel | 6 mg | 0.6% |
| Polyethylene Glycol 400 | 294 mg | 29.2% |
| Polysorbate 80 | 485 mg | 48.1% |
| Ethanol | 221 mg | 21.9% |
| Citric Acid | 2 mg | 0.2% |

Example 3

Animal pK Study of Paclitaxel Formulations

Two formulations of the present invention with the following compositions were prepared and used for PK studies in rats:

Sample V (Formulation V): 6 mg/mL paclitaxel dissolved in 29.4% Polyethylene Glycol 400, 52.9% Polysorbate 80, 17.6% Ethanol and 2.0 mg/mL citric acid.

Sample W (Formulation W): 6 mg/mL paclitaxel dissolved in 29.4% Polyethylene Glycol 400, 48.5% Polysorbate 80, 22.1% Ethanol and 2.0 mg/mL citric acid.

Both samples and the control (commercially available Taxol®) were diluted into sterile saline to a final concentration of 1 mg/mL before dosing. Six male Sprague-Dawley rats (7 weeks old, averaged 270 g each) from Charles River Japan were used per experimental group. Two single intravenous bolus doses (5 mg/kg and 10 mg/kg) were evaluated at an infusion rate of 1.5 mL/min. Plasma samples were collected at 0.083, 0.5, 1.0, 2.0, 3.0, 4.0, 8.0, and 24.0 hours post-dosing and stored at −20° C. until assayed with HPLC.

The pK profiles for each of the samples and the control were prepared, and are illustrated in FIGS. 1–4.

The results indicate that Samples V and W have very similar PK profiles in rats. The two formulations have lower AUC compared to the control, presumably due to the well-established non-linear pharmacokinetic interactions between paclitaxel and CREMOPHOR®.

All of the rats died in the control group (Taxol®) at 10 mg/kg dose. In comparison, all of the animals dosed with formulations V and W tolerated them well, even at the high dose of 10 mg/kg. These results suggest that Formulations V and W have improved safety in rats compared to TAXOL®.

The foregoing has demonstrated the pertinent and important features of the present invention. One of skill in the art will be appreciate that numerous modifications and embodiments may be devised. Therefore, it is intended that the appended claims cover all such modifications and embodiments.

What is claimed is:

1. A liquid pharmaceutical formulation for administration to a mammal comprising:
   (a) paclitaxel, a derivative, or a pharmaceutically acceptable salt thereof; and
   (b) two or more selected from the group consisting of a PEG-glyceryl fatty ester and a PEG-monoacid fatty ester:
   wherein said formulation is cremophor free.

2. The pharmaceutical formulation of claim 1, wherein:
   the PEG-glyceryl fatty ester is PEG-glyceryl monooleate or PEG-glyceryl monolaurate; and
   the PEG-monoacid fatty ester is PEG-20 monooleate, PEG-20 monolaurate, or PEG-20 monostearate.

3. The pharmaceutical formulation of claim 1, wherein said formulation is suitable for dissolution or reconstitution with an aqueous medium into a particulate-free solution suitable for parenteral administration.

4. The pharmaceutical formulation of claim 1, wherein per unit weight of the paclitaxel, the derivative, or the pharmaceutically acceptable salt thereof, a unit weight of the PEG-glyceryl fatty ester or the PEG-monoacid fatty ester ranges from about 5 to about 200.

5. The pharmaceutical formulation of claim 1, wherein said formulation is in liquid-concentrate form, and wherein a concentration of the PEG-glyceryl fatty ester or the PEG-monoacid fatty ester in the liquid-concentrate ranges from about 20 weight % to about 99 weight %.

6. The pharmaceutical formulation of claim 1, wherein said formulation further comprises an aqueous medium, and wherein a concentration of the PEG-glyceryl fatty ester or the PEG-monoacid fatty ester in the aqueous medium ranges from about 3 mg/ml to about 120 mg/ml.

7. The pharmaceutical formulation of 1, wherein the formulation is suitable for dissolution in an aqueous medium.

8. The pharmaceutical formulation of 1, wherein the formulation is in a liquid-concentrate form.

9. The pharmaceutical formulation of 1, wherein the formulation is suitable for parenteral administration.

10. The pharmaceutical formulation of 1, wherein the formulation is sterile.

11. The pharmaceutical formulation of 1, wherein the formulation is in single-unit-dosage form.

12. The pharmaceutical formulation of 1, wherein the formulation is in multi-unit-dosage form.

13. The pharmaceutical formulation of 1, wherein the formulation further comprising an additional excipient.

14. A liquid pharmaceutical formulation for administration to a mammal comprising paclitaxel, a derivative, or a pharmaceutically acceptable salt thereof; wherein said paclitaxel is solubilized by one or more solubilizer; and wherein said solubilizer, when included in an aqueous paclitaxel medium, can dissolve said paclitaxel at room temperature to a concentration of at least about 1.2 mg/ml water; and wherein said solubilizer is selected from the group consisting of: A PEG-monoacid fatty ester and a PEG-glyceryl fatty esters and wherein said formulation is cremophor free.

15. The pharmaceutical formulation of claim 14, wherein:
the PEG-glyceryl fatty ester is PEG-glyceryl monooleate or PEG-glyceryl monolaurate; and
the PEG-monoacid fatty ester is PEG-20 monooleate, PEG-20 monolaurate, or PEG-20 monostearate.

16. The pharmaceutical formulation of claim 14 further comprising ethanol.

17. The pharmaceutical formulation of claim 14, wherein said formulation is suitable for dissolution or reconstitution with an aqueous medium into a particulate-free solution suitable for parenteral administration.

18. The pharmaceutical formulation of claim 14, wherein per unit weight of the paclitaxel, the derivative, or the pharmaceutically acceptable salt thereof, a unit weight of the PEG-glyceryl fatty ester or the PEG-monoacid fatty ester ranges from about 5 to about 200.

19. The pharmaceutical formulation of claim 14, wherein said formulation is in liquid-concentrate form, and wherein a concentration of the PEG-glyceryl fatty ester or the PEG-monoacid fatty ester in the liquid-concentrate ranges from about 20 weight % to about 99 weight %.

20. The pharmaceutical formulation of claim 14, wherein said formulation further comprises an aqueous medium, and wherein a concentration of the PEG-glyceryl fatty ester or the PEG-monoacid fatty ester in the aqueous medium ranges from about 3 mg/ml to about 120 mg/ml.

21. The pharmaceutical formulation of claim 14, wherein the formulation is in a liquid-concentrate form.

22. The pharmaceutical formulation of claim 14, wherein the formulation is suitable for parenteral administration.

23. The pharmaceutical formulation of claim 14, wherein the formulation is sterile.

24. The pharmaceutical formulation of claim 14, wherein the formulation is in single-unit-dosage form.

25. The pharmaceutical formulation of claim 14, wherein the formulation is in multi-unit-dosage form.

26. The pharmaceutical formulation of claim 14, wherein the formulation further comprising an additional excipient.

27. A liquid pharmaceutical formulation for administration to a mammal consisting essentially of:
(a) paclitaxel, a derivative, or a pharmaceutically acceptable salt thereof; and
(b) two or more selected from the group consisting of a PEG-glyceryl fatty ester and a PEG-monoacid fatty ester.

28. A liquid pharmaceutical formulation for administration to a mammal consisting essentially of paclitaxel, a derivative, or a pharmaceutically acceptable salt thereof; and two or more solubilizers select d from the group consisting of a PEG-glyceryl fatty ester and a PEG-monoacid fatty ester; wherein said paclitaxel is solubilized by said one or more solubilizer; and wherein said solubilizer, when included in an aqueous paclitaxel medium, can dissolve said paclitaxel at room temperature to a concentration of at least about 1.2 mg/ml water.

* * * * *

UNITED STATES PATENT AND TRADEMARK OFFICE
CERTIFICATE OF CORRECTION

PATENT NO. : 6,919,370 B2
DATED : July 19, 2005
INVENTOR(S) : Hongming Chen

It is certified that error appears in the above-identified patent and that said Letters Patent is hereby corrected as shown below:

Column 38,
Line 16, "ester:" should read -- ester; --.
Lines 43, 46, 48, 50, 52, 54 and 56, "The pharmaceutical formulation of 1," should read -- The pharmaceutical formulation of claim 1, --.
Line 57, "further comprising" should read -- further comprises --.
Line 61, "one or more solubilizer;" should read -- one or more solubilizers; --.
Line 62, "said solubilizer," should read -- said solubilizer(s), --.
Line 64, "1.2 mg/ml water" should read -- 1.2 mg/ml in water --.
Line 65, "said solubilizer is" should read -- said solubilizer(s) is/are --.
Line 66, "consisting of: A PEG-" should read -- consisting of: a PEG- --.
Line 67, "esters and" should read -- ester; and --.

Column 39,
Line 6, "claim 14 further" should read -- claim 14, further --.

Column 40,
Line 1, "14 , wherein" should read -- 14, wherein --.
Line 10, "further comprising" should read -- further comprises --.
Line 21, "two or more solubilizers" should read -- one or more solubilizers --.
Line 21, "select d" should read -- selected --.
Line 24, "more solubilizer;" should read -- more solubilizers; --.
Line 24, "wherein said solubilizer," should read -- wherein said solubilizer(s), --.
Line 27, "1.2 mg/ml water" should read -- 1.2 mg/ml in water --.

Signed and Sealed this

Eighth Day of November, 2005

JON W. DUDAS
*Director of the United States Patent and Trademark Office*